United States Patent
Chen et al.

(10) Patent No.: US 11,685,898 B2
(45) Date of Patent: Jun. 27, 2023

(54) CARTILAGE-DERIVED MESENCHYMAL CELL LINES

(71) Applicant: Rhode Island Hospital, Providence, RI (US)

(72) Inventors: Qian Chen, Barrington, RI (US); Chathuraka T. Jayasuriya, Barrington, RI (US)

(73) Assignee: RHODE ISLAND HOSPITAL, Providence, RI (US)

( * ) Notice: Subject to any disclaimer, the term of this patent is extended or adjusted under 35 U.S.C. 154(b) by 961 days.

(21) Appl. No.: 16/081,029

(22) PCT Filed: Feb. 28, 2017

(86) PCT No.: PCT/US2017/019991
§ 371 (c)(1),
(2) Date: Aug. 29, 2018

(87) PCT Pub. No.: WO2017/151646
PCT Pub. Date: Sep. 8, 2017

(65) Prior Publication Data
US 2021/0198630 A1    Jul. 1, 2021

Related U.S. Application Data

(60) Provisional application No. 62/301,600, filed on Feb. 29, 2016.

(51) Int. Cl.
| | | |
|---|---|---|
| C12N 5/071 | (2010.01) | |
| C12N 5/077 | (2010.01) | |
| A61P 19/04 | (2006.01) | |
| A61K 35/32 | (2015.01) | |
| C12N 15/86 | (2006.01) | |
| G01N 33/50 | (2006.01) | |

(52) U.S. Cl.
CPC ............ *C12N 5/0655* (2013.01); *A61K 35/32* (2013.01); *A61P 19/04* (2018.01); *C12N 15/86* (2013.01); *G01N 33/5044* (2013.01); *C12N 2740/10043* (2013.01)

(58) Field of Classification Search
CPC .. C12N 5/0654; C12N 5/0655; C12N 5/0663; A61K 35/32
See application file for complete search history.

(56) References Cited

U.S. PATENT DOCUMENTS

| 2004/0241755 A1 | 12/2004 | Buckbinder et al. |
| 2015/0240208 A1 | 8/2015 | Noble et al. |

FOREIGN PATENT DOCUMENTS

| EP | 2716751 A1 | 4/2014 |
| WO | 2014/052912 A1 | 4/2014 |

OTHER PUBLICATIONS

Stringer, Bradley Michael John, 2004, US 20040180441 A1.*
West et al., 2014, US 20140178994 A1.*
Brittberg et al. "Clonal growth of human articular cartilage and the functional role of the periosteum in chondrogenesis." Osteoarthritis Cartilage. Feb. 2005;13(2):146-53.
Gen Bank Accession No. NM_000088, last updated on Aug. 4, 2018, located at <https://www.ncbi.nlm.nih.gov/nuccore/NM_000088.html> accessed on Aug. 29, 2018, 22 pages.
Gen Bank Accession No. NM_000118, last updated on Aug. 19, 2018, located at <https://www.ncbi.nlm.nih.gov/nuccore/NM_000118.html> accessed on Aug. 29, 2018, 6 pages.
Gen Bank Accession No. NM_000201, last updated on Jul. 22, 2018, located at <https://www.ncbi.nlm.nih.gov/nuccore/NM_000201.html> accessed on Aug. 29, 2018, 5 pages.
Gen Bank Accession No. NM_000346, last updated on Aug. 19, 2018, located at <https://www.ncbi.nlm.nih.gov/nuccore/NM_000346.html> accessed on Aug. 29, 2018, 5 pages.
Gen Bank Accession No. NM_000478, last updated on Aug. 19, 2018, located at <https://www.ncbi.nlm.nih.gov/nuccore/NM_000478.html> accessed on Aug. 29, 2018, 4 pages.
Gen Bank Accession No. NM_001078, last updated on Aug. 12, 2018, located at <https://www.ncbi.nlm.nih.gov/nuccore/NM_001078.html> accessed on Aug. 29, 2018, 5 pages.
Gen Bank Accession No. NM_001127708, last updated on Jun. 30, 2018, located at <https://www.ncbi.nlm.nih.gov/nuccore/NM_001127708.html> accessed on Aug. 29, 2018, 5 pages.
Gen Bank Accession No. NM_001135.3, last updated on Jul. 15, 2018, located at <https://www.ncbi.nlm.nih.gov/nuccore/NM_001135.html> accessed Aug. 29, 2018, 7 pages.
Gen Bank Accession No. NM_001243280, last updated on Jun. 25, 2018, located at <https://www.ncbi.nlm.nih.gov/nuccore/NM_001243280.html> accessed on Aug. 29, 2018, 5 pages.
Gen Bank Accession No. NM_001311160, last updated on Jul. 23, 2018, located at <https://www.ncbi.nlm.nih.gov/nuccore/NM_001311160.html> accessed on Aug. 29, 2018, 4 pages.
Gen Bank Accession No. NM_001844, last updated on Aug. 19, 2018, located at <https://www.ncbi.nlm.nih.gov/nuccore/NM_001844.html> accessed on Aug. 29, 2018, 12 pages.
Gen Bank Accession No. NM_002204, last updated on Aug. 26, 2018, located at <https://www.ncbi.nlm.nih.gov/nuccore/NM_002204.html> accessed on Aug. 29, 2018, 8 pages.
Gen Bank Accession No. NM_002211, last updated on Aug. 12, 2018, located at <https://www.ncbi.nlm.nih.gov/nuccore/NM_002211.html> accessed on Aug. 29, 2018, 7 pages.
Gen Bank Accession No. NM_002381, last updated on Aug. 19, 2018, located at <https://www.ncbi.nlm.nih.gov/nuccore/NM_002381.html> accessed on Aug. 29, 2018, 5 pages.

(Continued)

*Primary Examiner* — Shin Lin Chen
(74) *Attorney, Agent, or Firm* — Adler Pollock & Sheehan P.C.

(57) ABSTRACT

This invention is directed to, inter alia, stable cartilage-derived progenitor cell lines as well as methods for producing stable cartilage-derived progenitor cell lines from diseased human cartilaginous tissues and lesions. Also provided herein are methods for using cartilage-derived progenitor cell lines for treatment of cartilage and bone degenerative diseases.

2 Claims, No Drawings

Specification includes a Sequence Listing.

(56) References Cited

OTHER PUBLICATIONS

Gen Bank Accession No. NM_006902, last updated on Jul. 29, 2018, located at <https://www.ncbi.nlm.nih.gov/nuccore/NM_006902.html> accessed on Aug. 29, 2018, 5 pages.
Gen Bank Accession No. NP_000109, last updated on Aug. 19, 2018, located at <https://www.ncbi.nlm.nih.gov/protein/NP_000109.html> accessed on Aug. 29, 2018, 3 pages.
Gen Bank Accession No. NP_000192, last updated on Jul. 22, 2018, located at <https://www.ncbi.nlm.nih.gov/protein/NP_000192.html> accessed on Aug. 29, 2018, 3 pages.
Gen Bank Accession No. NP_000337, last updated on Aug. 19, 2018, located at <https://www.ncbi.nlm.nih.gov/protein_NP_000337.html> accessed on Aug. 29, 2018, 3 pages.
Gen Bank Accession No. NP_000469, last updated on Aug. 19, 2018, located at <https://www.ncbi.nlm.nih.gov/protein/NP_000469.html> accessed on Aug. 29, 2018, 3, pages.
Gen Bank Accession No. NP_001069, last updated on Aug. 12, 2018, located at <https://www.ncbi.nlm.nih.gov/protein/NP_001069.html> accessed on Aug. 29, 2018, 3 pages.
Gen Bank Accession No. NP_001121180, last updated on Jun. 30, 2018, located at <https://www.ncbi.nlm.nih.gov/protein/NP_001121180.html> accessed on Aug. 29, 2018, 3 pages.
Gen Bank Accession No. NP_001126, last updated on Jul. 15, 2018, located at <https://www.ncbi.nlm.nih.gov/protein/NP_001126.html> accessed on Aug. 29, 2018, 4 pages.
Gen Bank Accession No. NP_001230209, last updated on Jun. 25, 2018, located at <https://www.ncbi.nlm.nih.gov/protein/NP_00123209.html> accessed on Aug. 29, 2018, 3 pages.
Gen Bank Accession No. NP_001298089, last updated on Jul. 23, 2018, located at <https://www.ncbi.nlm.nih.gov/protein/NP_001298089.html> accessed on Aug. 29, 2018, 3 pages.
Gen Bank Accession No. NP_001835, last updated on Aug. 19, 2018, located at <https://www.ncbi.nlm.nih.gov/protein/NP_001835.html> accessed on Aug. 29, 2018, 6 pages.
Gen Bank Accession No. NP_002195, last updated on Aug. 26, 2018, located at <https://www.ncbi.nlm.nih.gov/protein/NP_002195.html> accessed on Aug. 29, 2018, 4 pages.
Gen Bank Accession No. NP_002202 last updated on Aug. 12, 2018, located at <https://www.ncbi.nlm.nih.gov/protein/NP_002202.html> accessed on Aug. 29, 2018, 4 pages.
Gen Bank Accession No. NP_002372, last updated on Aug. 19, 2018, located at <https://www.ncbi.nlm.nih.gov/protein/NP_002372.html> accessed on Aug. 29, 2018, 3 pages.
Gen Bank Accession No. NP_008833, last updated on Jul. 29, 2018, located at <https://www.ncbi.nlm.nih.gov/protein/NP_008833.html> accessed on Aug. 29, 2018, 3 pages.
International Search Report and Written Opinion issued in International Patent Application No. PCT/US17/019991, dated Sep. 6, 2017. 13 pages.
UniProt Accession No. P02452, last updated on Jul. 18, 2018, located at <https://www.uniprot.org/uniprot/P02452.txt> accessed on Aug. 29, 2018, 34 pages.
Dowthwaite et al. (Feb. 29, 2004) "The Surface of Articular Cartilage Contains a Progenitor Cell Population", Journal of Cell Science, 117(Pt 6):889-897.
Williams et al. (Oct. 14, 2010) "Identification and Clonal Characterisation of a Progenitor Cell Sub-Population in Normal Human Articular Cartilage", PLos One, e13246, 5(10):14 pages.
Hu, N., Gao, Y., Jayasuriya, C.T. et al. Chondrogenic induction of human osteoarthritic cartilage-derived mesenchymal stem cells activates mineralization and hypertrophic and osteogenic gene expression through a mechanomiR. Arthritis Res Ther 21, 167 (2019). https://doi.org/10.1186/s13075-019-1949-0.
Liu W, Brodsky AS, Feng M, Liu Y, Ding J, Jayasuriya CT and Chen Q, Senescent Tissue-Resident Mesenchymal Stromal Cells Are an Internal Source of Inflammation in Human Osteoarthritic Cartilage. Front. Cell Dev. Biol. (2021). 9:725071. doi: 10.3389/fcell.2021.725071.
Liu, W., Feng, M., Jayasuriya, C. T., Peng, H., Zhang, L., Guan, Y., et al. (2020). Human osteoarthritis cartilage-derived stromal cells activate joint degeneration through TGF-beta lateral signaling. FASEB J. 34, 16552-16566. doi: 10.1096/fj.202001448R.
"Extended European Search Report received for EP Patent Application No. 17760633.2, dated Sep. 19, 2019", 7 pages.
Kozhemyakina, et al., "Identification of a Prg4-Expressing Articular Cartilage Progenitor Cell Population in Mice", Arthritis & Rheumatology, vol. 67, No. 5, May 2015, pp. 1261-1273.
Seol, et al., "Chondrogenic Progenitor Cells Respond to Cartilage Injury", Arthritis & Rheumatism, vol. 64, No. 11, Nov. 2012, pp. 3626-3637.

* cited by examiner

CARTILAGE-DERIVED MESENCHYMAL CELL LINES

CROSS-REFERENCE TO RELATED APPLICATIONS

This application is a national stage application filed under 35 U.S.C. § 371 of International Patent Application No. PCT/US2017/019991, filed Feb. 28, 2017, which claims the benefit of priority to U.S. Provisional Patent Application No. 62/301,600, filed Feb. 29, 2016, the entire contents of each of which are incorporated by reference herein for all purposes.

STATEMENT OF GOVERNMENT INTERESTS

The invention was made with government support under P20 GM104937 awarded by National Institutes of Health. The government has certain rights in the invention.

INCORPORATION BY REFERENCE OF SEQUENCE LISTING

The contents of the text file named "021486-628N01US_Sequence_Listing_ST25", which was created on Aug. 28, 2018, and is 4,722 bytes in size, are hereby incorporated by reference in their entireties and for all purposes.

FIELD OF INVENTION

This invention is directed to, inter alia, cartilage-derived progenitor cell lines, methods for isolating the same from sources of diseased cartilage, as well as methods for using the same for treating degenerative diseases of connective tissues including cartilage, meniscus, skin, muscle, synovium, tendon, ligament, blood vessels, and bone.

BACKGROUND

Degenerative diseases of cartilage, including joint and disc diseases such as osteoarthritis and rheumatoid arthritis are widespread. Early symptoms common to these diseases include progressive loss of proteoglycans in the joint (as evidenced by loss of metachromasia); collagen degradation; fibrillation of the cartilage surface; osteophyte formation, subchondral bone sclerosis, and, ultimately, loss of cartilage. Meniscus injuries commonly occur in athletes and military service men/women. Meniscal injuries cause destabilization of the knee and often lead to the chronic onset of post-traumatic osteoarthritis.

Cartilage-derived progenitors are a recently discovered and very sparse population of progenitor cells that show promise for potential use in cartilage defect therapy and degenerative joint disease therapy. Since they are so few in number, normally they must be isolated from tissue and extensively expanded to produce sufficient cell numbers before they can be used for research or therapeutic purposes. The expansion process not only takes weeks to complete, but it can reduce the "sternness" and colony forming efficiency of these cells. As such, new and improved methods for producing stable cartilage-derived progenitor cell lines are required to circumvent these problems.

SUMMARY

The invention provides a solution to difficulties associated with earlier methods and cell populations. Accordingly, the inventions includes stable cartilage-derived progenitor cell lines as well as methods for producing the same by first extracting cells ex vivo or in vitro from diseased human cartilage enzymatically to release cells from the dense tissue matrix. Progenitor cells are enriched by differential adhesion to fibronectin and then stabilized using a retroviral vector carrying T-Antigen. Also provided herein are methods for using cartilage-derived progenitor cell lines for the treatment of meniscal injuries, bone and cartilage degenerative diseases as well as methods for using these cells to screen for candidate compounds for treating meniscal injuries and one or more cartilage and/or bone degenerative disorders.

Accordingly, in some aspects, provided herein are methods for producing a stable cartilage-derived progenitor cell line, the method comprising: enzymatically digesting cartilaginous tissue to release cells from the cartilaginous tissue matrix, wherein the cartilaginous tissue is obtained from an individual diagnosed with a cartilage-related disease; enriching the cells by differential adhesion to fibronectin in culture; and stabilizing the cells by infection with an SV-40 retroviral vector. In some embodiments, the individual is diagnosed with osteoarthritis, post-traumatic osteoarthritis, rheumatoid arthritis, chondromatosis, costochondritis, relapsing polychondritis, herniation, chondrolysis, achondroplasia, chondrodysplasia, chondroma, chondrosarcoma, growth plate fracture and deformity, bone fracture, bone cyst, bone spur (osteophytes), bone tumor, craniosynostosis, fibrodysplasia ossificans progressive, myositis ossificans, progressive osseous heteroplasia, fibrous dysplasia, hypophosphatasia, metabolic bone disease, heterotopic ossification, vascular calcification/ossification, Paget's disease of bone, osteochondritis dissecans, osteogenesis imperfect, osteomalacia, osteopenia, osteoporosis, or osteopetrosis. In some embodiments of any of the embodiments disclosed herein, the cells are digested using the enzyme(s) pronase and/or collagenase. In some embodiments of any of the embodiments disclosed herein, the individual is a human being. In other examples, the individual is a mouse, rat, companion animal, such as a dog or cat or working/performance animal such as a horse or cow. In some embodiments of any of the embodiments disclosed herein, the stabilized cells express less aggrecan (ACAN), type II collagen (COL2A1), (SRY-box 9) SOX9, matrilin-3 (MATN3), and/or lubricin (PRG4) relative to chondrocytes derived from healthy adult tissue. In some embodiments of any of the embodiments disclosed herein, the stabilized cells express comparable levels of SOX9, MATN3, and/or PRG4 relative to bone marrow-derived mesenchymal stem cells (BM-MSCs). In some embodiments of any of the embodiments disclosed herein, the stabilized cells express less or comparable level of type I collagen (COL1) relative to BM-MSCs. In some embodiments of any of the embodiments disclosed herein, the stabilized cells express one or more mesenchymal cell surface markers selected from the group consisting of CD29, CD49c, CD105, and CD166. In some embodiments of any of the embodiments disclosed herein, the stabilized cells do not express the BM-MSC cell surface marker stage-specific embryonic antigen 4 (SSEA4). In some embodiments of any of the embodiments disclosed herein, the stabilized cells express the chondrocyte cell surface marker CD54. In some embodiments of any of the embodiments disclosed herein, the stabilized cells do not express the chondrocyte cell surface marker CD106. In some embodiments of any of the embodiments disclosed herein, the stable cartilage-derived progenitor cell line is a chondroprogenitor cell line or an osteochondro-progenitor cell line. In some embodiments of any of the embodiments disclosed herein, the osteochondro-progenitor cell line expresses more transcription factor Paired related homeobox 1 (PRX1) relative to the chondroprogenitor cell line. In some embodiments of any of the embodiments disclosed herein, the osteochondro-progenitor cell line expresses about at least 10%, 20%, 50%, 75%, or 2-fold, 3-fold, 4-fold, 5-fold or 10-fold or more PRX1 relative to the chondroprogenitor cell line. In some embodiments of any of the embodiments disclosed herein, the osteochondro-progenitor cell line expresses more of the mesenchymal cell surface marker CD90 relative to the chondroprogenitor cell line. In some embodiments of any of the embodiments disclosed herein, the chondroprogenitor cell line exhibits higher Safranin-O staining upon induction with chondrocyte differentiation medium relative to the osteochondro-progenitor cell line. In some embodiments of any of the embodiments disclosed herein, the chondroprogenitor cell line expresses one or more long non-coding RNA molecules selected from the group consisting of FAM86, 10324 and TVAS5. In some embodiments of any of the embodiments disclosed herein, the osteochondro-progenitor cell line exhibits a) higher Alizarin Red staining; and b) higher expression of alkaline phosphatase (ALPL) upon induction with osteogenesis differentiation medium relative to the chondroprogenitor cell line. In some embodiments of any of the embodiments disclosed herein, the osteochondro-progenitor cell line and the chondroprogenitor cell line both exhibit moderate Oil Red O staining in response to induction with adipogenic medium.

In other aspects, provided herein are stable chondroprogenitor cell lines produced by the methods disclosed herein. In other aspects, provided herein are stable osteochondroprogenitor cell lines produced by the methods disclosed herein. In some embodiments of any of the embodiments disclosed herein, the cells express at least 10%, 20%, 50%, 75%, or 2-fold, 3-fold, 4-fold, 5-fold or 10-fold or more less aggrecan (ACAN), type II collagen (COL2A1), SOX9, matrilin-3 (MATN3), and/or lubricin (PRG4) relative to chondrocytes derived from healthy adult tissue. In some embodiments, the cells express comparable levels (e.g. within 10% difference or less) of SOX9, MATN3, and/or PRG4 relative to bone marrow-derived mesenchymal stem cells (BM-MSCs). In some embodiments of any of the embodiments disclosed herein, the cells express less type I collagen (COL1) relative to BM-MSCs. In some embodiments of any of the embodiments disclosed herein, the cells express one or more mesenchymal cell surface markers selected from the group consisting of CD29, CD49c, CD105, and CD166. In some embodiments of any of the embodiments disclosed herein, the cells do not express the BM-MSC cell surface marker SSEA4. In some embodiments of any of the embodiments disclosed herein, the cells express the chondrocyte cell surface marker CD54. In some embodiments of any of the embodiments disclosed herein, the cells do not express the chondrocyte cell surface marker CD106. In some embodiments, the cell line is CPCL2. In some embodiments, the cell line is CPCL18.

In further aspects, provided herein are methods for repairing or regenerating cartilaginous tissue in an individual in need thereof, said method comprising administering cells from the stable chondroprogenitor cell lines or osteo-progenitor or chondro-progenitor cell lines disclosed herein to the individual. In some embodiments, the individual to whom the cells will be administered has suffered a meniscal injury. In some embodiments, the degenerative cartilage disease is selected from the group consisting of osteoarthritis, osteoarthrosis, degenerative diseases of the joints, collagen deficiencies, cartilage or bone diseases characterized by endochondrial ossifications, polychondritis, degenerative disc diseases, achondroplasty, costochondritis, rheumatoid arthritis, juvenile arthritis, undifferentiated chronic arthritis, polyarthritis, intervertebral disc herniation, ankylosing spondylitis, secondary arthritis of autoimmune origin, systemic lupus erythematosus arthritis, psoriasic arthritis, Crohn's disease arthritis, arthritis of dysmetabolic origin, monosodium urate arthropathy, pyrophosphate arthropathy, traumatic rupture or detachment of cartilage, calcium oxalate arthropathy, chondrodystrophies, infectious arthritis, arthritis due to osteoporosis, aseptic osteonecrosis, and benign and malignant bone tumors. In some embodiments of any of the embodiments disclosed herein, the individual is a human being.

In another aspect, provided herein are methods for treating a degenerative bone disease in an individual in need thereof, said method comprising administering cells from the stable osteochondro-progenitor cell lines provided herein to the individual. In some embodiments, the degenerative bone disease is selected from the group consisting of fracture, osteoporosis, osteopenia, Paget's disease, malignant bone disease, bone degeneration due to hyperparathyroidism, and other conditions associated with increased bone resorption or turnover. In some embodiments of any of the embodiments disclosed herein, the individual is a human being.

In yet other aspects, provided herein are methods for identifying a compound capable of inhibition of osteophyte formation and/or promotion of chondrogenesis, the method comprising contacting any of the cells or cell lines disclosed herein with the compound; and assessing whether the compound inhibits osteophyte formation and/or promotes chondrogenesis. In some embodiments, the compound is one or more compounds selected from the group consisting of small molecule chemical compounds, antibodies, proteins, inhibitory nucleic acids, and any combination thereof.

In other aspects, provided herein are kits comprising any of the cells or cell lines provided herein and written instructions for using the cells for screening for candidate compounds capable of inhibition of osteophyte formation, inhibition of cell hypertrophy markers RUNX2 and type X collagen, and/or promotion of chondrogenesis. In some embodiments, the kits further comprise a mammalian cell culture medium.

In further aspects, provided herein is a stable chondroprogenitor cell line that expresses less aggrecan (ACAN), type II collagen (COL2A1), SOX9, matrilin-3 (MATN3), and/or lubricin (PRG4) relative to chondrocytes derived from healthy adult tissue. In additional aspects, provided herein is a stable osteochondroprogenitor cell line that expresses less aggrecan (ACAN), type II collagen (COL2A1), SOX9, matrilin-3 (MATN3), and/or lubricin (PRG4) relative to chondrocytes derived from healthy adult tissue. In yet other aspects, provided herein is a stable osteochondroprogenitor cell line that expresses less SOX9, aggrecan (ACAN), paired related homeobox 1 (PRX1) and/or Type X collagen relative to chondrocytes derived from healthy adult tissue. In some embodiments of any of the embodiments disclosed herein, the cells express comparable levels of SOX9, MATN3, and/or PRG4 relative to bone marrow-derived mesenchymal stem cells (BM-MSCs). In some embodiments, the cells express less type I collagen (COL1) relative to BM-MSCs. In some embodiments of any of the embodiments disclosed herein, the cells express one or more mesenchymal cell surface markers selected from the group consisting of CD29, CD49c, CD105, and CD166. In some embodiments of any of the embodiments disclosed herein, the cells do not express the BM-MSC cell surface marker SSEA4. In some embodiments of any of the embodiments disclosed herein, the cells express the chondrocyte cell surface marker CD54. In some embodiments of any of the embodiments disclosed herein, the cells do not express the chondrocyte cell surface marker CD106. In some embodiments, the cells express less type I collagen (COL1) relative to chondrocytes derived from healthy adult tissue. In some embodiments of any of the embodiments disclosed herein, the cells express higher amounts of ACAN relative to BM-MSCs. In some embodiments of any of the embodiments disclosed herein, the cells express less PRX and/or Type X collagen relative to BM-MSCs. In some embodiments of any of the embodiments disclosed herein, the cell line is derived from tissue from an individual diagnosed with osteoarthritis (OA). In some embodiments of any of the embodiments disclosed herein, the cell line is derived from tissue from an individual diagnosed with osteosarcoma. In some embodiments of any of the embodiments disclosed herein, the cell line is CPCL2. In some embodiments of any of the embodiments disclosed herein, the cell line is CPCL1. In some embodiments of any of the embodiments disclosed herein, the cell line is CPCL14. In some embodiments of any of the embodiments disclosed herein, the cell line is NCPCL3. In some embodiments of any of the embodiments disclosed herein, the cell line is CPCL18. In some embodiments of any of the embodiments described herein, the cell line is selected from the group of cell lines consisting of CPCL1, CPCL14, and NCPCL3 deposited with the American Type Culture Collection (ATCC) under Accession Numbers PTA-124029, PTA-124018, and PTA-124019, respectively. In some embodiments of any of the embodiments disclosed herein, the cells express one or more mesenchymal cell surface markers selected from the group consisting of CD29, CD49c, CD105, and CD166. In some embodiments of any of the embodiments disclosed herein, the stabilized cells do not express the BM-MSC cell surface marker SSEA4. In some embodiments of any of the embodiments disclosed herein, the stabilized cells express the chondrocyte cell surface marker CD54.

In another aspect, provided herein is a cell line is selected from the group of cell lines consisting of CPCL1, CPCL14, and NCPCL3 deposited with the American Type Culture Collection (ATCC) under Accession Numbers PTA-124029, PTA-124018, and PTA-124019, respectively.

Each of the aspects and embodiments described herein are capable of being used together, unless excluded either explicitly or clearly from the context of the embodiment or aspect.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

BRIEF DESCRIPTION OF THE DRAWINGS

FIG. 1 is an illustration of human adult cartilage-derived progenitor subpopulations isolated, enriched and stabilized to generate cell lines.

FIG. 2A is a bar graph showing quantification of CD49e and COL2A1 mRNA levels in primary human chondroprogenitor cells (CPC), compared with primary human chondrocytes (PHC). FIG. 2B is a graph showing relative aggrecan (ACAN) mRNA expression levels, FIG. 2C is a graph showing type II collagen (COL2A1) mRNA expression levels and FIG. 2D is a graph showing fibronectin receptor CD49e mRNA expression levels in human articular chondrocytes and nine chondroprogenitor cell lines (CPCL). Chondroprogenitor cell lines were categorized into two groups (GI, GII) based on their relative ACAN and COL2A1 expression levels. Due to the wide distribution of relative expression values, a logarithmic scale on the y-axis is implemented for each tested marker in B-D. n≥3. *p≤0.05; **p≤0.01, relative to the chondrocyte control group.

FIG. 3A is a bar graph showing relative mRNA expression of transcription factor PRX1; FIG. 3B is a bar graph showing relative mRNA expression of transcription factor SOX9; FIG. 3C depicts relative mRNA expression of cartilage matrix protein matrilin-3; FIG. 3D is a bar graph showing relative mRNA expression of fibroblast marker COL I; and FIG. 3E is a bar graph showing relative mRNA expression of cartilage surface lubricating protein PRG4 in mature articular chondrocytes, BM-MSCs, CPCL2 and CPCL18. p≥3. #p≤0.05, relative to the BM-MSCs group. * p≤0.05, relative to the chondrocyte group.

FIG. 4A are graphs depicting a representative flow cytometry analysis for surface expression markers on CPCL2. FIG. 4B are graphs depicting a representative flow cytometry for surface expression markers on CPCL18. Empty peaks indicate the results obtained from cells stained with isotype control antibodies and filled peaks indicate the results of cells stained with specific target antibodies. FIG. 4C is a bar graph showing the compiled results of flow cytometry experiments for surface expression markers using BM-MSCS, chondrocytes, CPCL2 and CPCL18. N≥3. #p≤0.05, relative to the BM-MSCs group. * p≤0.05, relative to the chondrocyte group.

FIG. 5A is a micrograph showing pellet cultures of CPCL2 (OA-SCL2) and CPCL18 (OA-SCL18) were sectioned, stained with Safranin 0 after 21 days of induction with chondrogenesis medium and imaged at 20× magnification. FIG. 5B are bar graphs showing quantification of ACAN, COL2A1, SOX9 and COL10A1 (top) and collagen X (bottom) mRNA expression in monolayer culture following chondrogenesis induction. Non-induction control groups were cultured in monolayer. FIG. 5C are graphs depicting the relative fold change in MMP-13 protein level in CPCL2 and CPCL18 following 3, 7 and 14 days in chondrogenesis medium, compared with growth medium. Protein levels were quantified by ELISA. FIG. 5D shows a micrograph of osteogenic induction of CPCL2 and CPCL18 for 21 days followed by Alizaran Red staining. Images were taken at 4× magnification. FIG. 5E are bar graphs depicting quantification of ALPL mRNA expression. FIG. 5F shows micrographs depicting adipogenic induction of CPCL2 and CPCL18 for 21 days followed by Oil Red O staining. Images were taken at 10× magnification. FIG. 5G are bar graphs showing quantification of LPL mRNA expression following adipogenesis induction. n≥3. * p≤0.05, relative to respective control groups cultured in growth media. FIG. 5H is a line graph depicting cell proliferation rate of CPCL2 and CPCL18 was determined by quantifying viable cell number that results from culturing each cell line for 6 days in chondroprogenitor growth medium or osteogenesis induction medium.

FIG. 6A is a bar graph showing LncRNA expression changes during MSCs differentiation into chondrocytes. RNAs were collected 21 days after induction of chondrogenesis and quantified by qRT-PCR. FIG. 6B is a bar graph showing, after chondrogenic induction, expression of chondrogenic-specific markers showed higher levels in Line 2 and Line 18. FIG. 6C is a bar graph showing expression of lncRNAs in Line 2 and Line 18 after induction. Values for control samples were normalized to 1 for each individual lncRNA or mRNA. Experiments were performed in triplicate, and error bars represent SD in all panels.

FIG. 7 is a micrograph showing cellular morphologies of CPCL2, CPCL18, mature articular chondrocytes (PHCs) and bone marrow derived mesenchymal stem cells (BM-MSCs). Images were acquired at 10× magnification using an inverted microscope.

FIG. 8A is an image of immunofluorescent staining of human OA cartilage sections with an antibody against CD166 and FIG. 8B is an image showing an antibody against PRG4. White arrows indicate some positive staining events. FIG. 8C is an image showing a control section stained with secondary antibody alone. FIG. 8D is a bar graph showing quantification of ACAN, FIG. 8E is a bar graph showing quantification of COL2A1 and FIG. 8F is a bar graph showing quantification of CD49e mRNA levels in CD166+ primary human chondroprogenitors (OA stem cells), compared with CD166− primary human chondrocytes. n≥3. **, p≤0.01, relative to CD166− chondrocyte group.

FIG. 9 is an illustration showing osteochondral-progenitor and chondroprogenitor cell lineage. The development of osteochondral-progenitors and chondroprogenitors may occur sequentially along the same lineage in two stages (left) or in a parallel fashion along two separate lineages (right). Information gathered from the molecular marker-based characterization of each progenitor cell type analyzed is summarized in the diagram.

FIG. 10A is a pictograph showing immunofluorescent staining of human OA cartilage sections with an antibody against CD166+ showing single OA stem cells as well as stem cell clusters (left panels). OA chondrocytes and chondrocyte clusters were negative for CD166 (right panels). DAPI was used as a nuclear stain to visualize all cells. FIG. 10B, FIG. 10C, and FIG. 10D depict the relative frequency of single cells, 2-cell clusters, 3-cell clusters, and greater than 3-cell clusters of CD166+ and CD166− cells in OA cartilage sections from 3 different patients, respectively. The histological grade of each patient sample is indicated according to the OARSI scoring system.

FIG. 11 is a bar graph depicting mRNA quantification of SOX-9 (FIG. 11A) aggrecan (FIG. 11B), type I collagen (FIG. 11C), PRX1 (FIG. 11D) and type X collagen (FIG. 11E) in eight non-diseased cartilage-derived chondroprogenitor cell lines (nCPCL), compared with primary human chondrocytes and human bone marrow-derived mesenchymal stem cells (BM-MSCs). n≥3. *, P≤0.05 relative to chondrocytes. #, P≤0.05 relative to BM-MSCs.

FIG. 12A depicts a diagram of the meniscus. The meniscus is divided into vascular (dark), semi-vascular (light) and avascular (white) regions. The inner region heals poorly due to its avascularity and presents a significant clinical challenge. FIG. 12B depicts an image of CD90−/CD105+/CD166+ cartilage-derived progenitors (fluorescently labeled) demonstrating their adherence to the avascular inner meniscus following 4 days in meniscus organ culture. Image was obtained using an inverted microscope at 10× original magnification. FIG. 12C depicts confocal microscope images of a sectioned decellularized rat meniscus 4 weeks after being seeded with CD90−/CD105+/CD166− cartilage progenitors. DAPI nuclear staining indicates that the cells largely integrated into the inner meniscus. FIG. 12D depicts Saf-O staining of the avascular region of sectioned decellularized rat meniscus 4 weeks after being seeded with CD90−/CD105+/CD166− cartilage progenitors. Left panel: No cell (control); Right panel: seeded with cartilage progenitors. The cells increase the proteoglycan content in the meniscus as indicated by the stronger staining in the right side panel, compared to left side control. Arrows signify stem cells that have integrated into the inner meniscus.

FIG. 13A is a pictograph showing $5.0 \times 10^5$ cartilage-derived progenitor cells (left panel) and $5.0 \times 10^5$ BM-MSCs (right panel) fluorescently labeled and cultured with a rat meniscus containing a radial incision (indicated by arrowhead and circumscribed in white) for 72 hours in a 96-microwell plate. Cells appear to migrate to the area of the incision. FIG. 13B depicts an mRNA expression analysis indicating that human collagen I gene expression levels between cartilage-derived progenitor cells and BM-MSCs, following 4-week culture in meniscus, is comparable. There is no significant difference between collagen I expression by these cells. However, FIG. 13C depicts that collagen X expression is significantly higher in the BM-MSC group. n≥3. *, P≤0.05 relative to nCPCL1 group.

DETAILED DESCRIPTION

The invention described herein provides, inter alia, cartilage-derived progenitor cells and cell lines derived from diseased cartilage tissue or an individual comprising a diseased cartilage tissue as well as methods for deriving and culturing the same. Since cartilage-derived progenitors are sparse in cartilage tissue, obtaining sufficient cell numbers for research or for use in treating diseases related to pathological degeneration of cartilage can be a time consuming and labor intensive. The inventors of the present application have surprisingly discovered that normal cartilage collected during the course of treating diseases such as musculoskeletal sarcomas and osteoarthritis is a viable cell source of cartilage-derived stem cells. Patients presenting with diseases such as chondrosarcoma and osteosarcoma sometimes require amputation or removal of the diseased tissue. During these surgeries, some non-diseased tissue (which borders or remains adjacent to the diseased tissue) is also removed as a precaution to ensure that the entirety of the tumor is removed. As will be described in more detail herein, this normal cartilage bordering otherwise diseased tissue can serve as a source for the cartilage-derived stem cell lines disclosed herein.

The methods for producing stable cartilage-derived progenitor cell lines described herein can produce an abundant progenitor population that can be extensively expanded while retaining the stem cell-like properties of the progenitor cells. Furthermore, unlike freshly isolated primary cartilage-derived progenitors, which need to be sorted to verify their identity, each individual cell line generated using the methods disclosed herein represents a single pure progenitor population and not a heterogeneous mixed population. As such, the cartilage-derived progenitor cells and cell lines obtained by the methods disclosed herein can provide a ready source of stable chondroprogenitor cell subpopulations for basic and translational scientific research purposes, including drug screening. Further, the cartilage-derived progenitor cells disclosed herein can be used in conjunction with preexisting bioengineereing and regenerative medicine approaches to repair damaged and/or diseased cartilage and bone tissue.

I. Definitions

"Cartilage," or "cartilaginous tissue," as used herein, encompasses articular cartilage, hyaline cartilage, neocartilage, devitalized cartilage, auricular cartilage, cartilage from an autogenous source, cartilage from an allogenic source, cartilage from a xenogeneic source, juvenile cartilage, tissue from the transient cartilaginous phase during bone formation and regeneration, or a combination thereof. The term "cartilaginous tissue" includes permanent as well as transient cartilage. For example, permanent cartilage includes or refers to articular cartilage, e.g., cartilage present at the interface between articulating bones such as knee, elbow, shoulder, spine, hip, finger, and/or toe bones. Transient cartilaginous tissue includes cartilage present in the growth plate of developing bone, e.g., cartilage that forms a template for bone in growing mammals such as humans. For example, a growth plate maintains a cartilaginous state up until the individual attains skeletal maturity, typically at the age of 16-25 years of age. Transient cartilaginous tissue also encompasses cartilage of regenerating bone, e.g., bone tissue that has been stressed, compromised, or injured, e.g., by a bone fracture, in an adult or juvenile individual. Bone regeneration in such circumstances, e.g., bone fracture healing, recapitulates bone development. For example, healing of a fractured bone includes a cartilage phase (cartilaginous tissue), which is then remodeled, resulting in healing and replacement of bone tissue at the site of the incident of bone stress, injury, or fracture.

The term "meniscus" refers to soft fibrocartilagenous piece of tissue that provides stability in a joint (such as, but not limited to, the knee joint).

The term "cartilage-related disease" refers to a structural and/or biological imperfection in cartilage or bone (osseous) tissue such as but not limited to a break, tear, void or other disintegration of the tissue, which is caused by a disease, injury or condition and which can benefit from cartilage repair, replacement, or augmentation, such as, in non-limiting example, athletic injury, traumatic injury, congenital disorders, osteoarthritis and/or pathologic joint degeneration. In some embodiments, non-limiting examples of phenotypic indicators of cartilage-related disease include proteoglycan loss, joint space narrowing, collagen degradation, and destruction of cartilage. In one embodiment, a cartilage-related disease does not encompass cartilage degeneration due to aging. In other embodiments, cartilage-related disease refers to one or more of post-traumatic osteoarthritis, rheumatoid arthritis, chondromatosis, costochondritis, relapsing polychondritis, herniation, chondrolysis, achondroplasia, chondrodysplasia, chondroma, chondrosarcoma, growth plate fracture and deformity, bone fracture, bone cyst, bone spur (osteophytes), bone tumor (e.g., osteosarcoma), craniosynostosis, fibrodysplasia ossificans progressive, fibrous dysplasia, hypophosphatasia, metabolic bone disease, Paget's disease of bone, osteochondritis dissecans, osteogenesis imperfect, osteomalacia, osteopenia, osteoporosis, or osteopetrosis. Thus, the cells and cell lines described herein are useful for treating not only degenerative orthopedic disorders, but also developmental diseases, e.g., those associated with pediatric orthopedic disorders, as well as bone regeneration disorders and bone fracture healing.

A "stem cell," as used herein, refers to a cell that can continuously produce unaltered progeny and which also has the ability to produce progeny cells that have different and more restricted properties.

The phrase "progenitor cell" refers to a dividing cell with the capacity to differentiate, which includes putative stem cells in which self-renewal has not yet been demonstrated.

A "cartilage-derived progenitor cell" has the ability to differentiate into osteoblasts or chondrocytes, depending on the signaling molecules they are exposed to, giving rise to either bone or cartilage respectively.

As used herein, "cell line," refers to a population of cells capable of continuous or prolonged growth and division in vitro. Often, cell lines are clonal populations derived from a single progenitor cell. It is further known in the art that spontaneous or induced changes can occur in the genotype during storage or cell lines. Therefore, cells derived from a cell line may not be precisely identical to the ancestral cells or cultures, and the cell line(s) referred to herein includes such variants. The term "cell lines" also includes immortalized cells, such as cells immortalized with one or more viral vectors (such as SV40). In some embodiments, cell lines are distinguished from other types of cells (such as populations of progenitor cells) by a cell line's ability to grow and divide continuously for a prolonged (such as an infinite) period of time.

An "individual" can be a vertebrate, a mammal, or a human. Mammals include, but are not limited to, farm animals, sport animals, pets, primates, mice and rats. In one aspect, an individual is a human.

As used herein, "repairing cartilaginous tissue" means promoting tissue repair, growth, and/or maintenance including, but not limited to, wound repair or tissue engineering.

As used herein, "regenerating cartilaginous tissue" refers to replacing lost, diseased or otherwise damaged tissue by the formation of new tissue.

"Treatment," "treat," or "treating," as used herein covers any treatment of a disease or condition of a mammal, for example, a human, and includes, without limitation: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of individuals treated by the methods of the invention includes individuals suffering from the undesirable condition or disease, as well as individuals at risk for development of the condition or disease.

As used herein, a "injury" is any disruption, from whatever cause, of normal anatomy (internal and/or external anatomy) including but not limited to traumatic injuries such as mechanical (i.e. contusion, penetrating, crush), thermal, chemical, electrical, radiation, concussive and incisional injuries; elective injuries such as operative surgery and resultant incisional hernias, fistulas, etc.; acute injuries, chronic injuries, infected injuries, and sterile injuries.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

II. Methods of the Invention

A. Generation of Stable Cartilage-Derived Progenitor Cell Lines

Provided herein are methods for producing a stable cartilage-derived progenitor cell line. The source material for these progenitor cells is diseased cartilage tissue or normal cartilage tissue isolated from an individual diagnosed with a cartilaginous disease or lesion. This tissue can be obtained from any number of sources including, without limitation, from cartilage or bone biopsies performed on live individuals. In one embodiment, the source cartilaginous tissue is isolated from a human individual. In humans, the source of diseased cartilage tissue for use in any of the methods disclosed herein can be from a joint, such as the knee joint, hip elbow, or shoulder. In some embodiments, the cartilage can be obtained via biopsy using arthroscopy. Cartilage tissue can be isolated from a cartilage biopsy using diverse methods commonly known in the art.

Suitable sources of cartilage tissue for use in the methods described herein include, without limitation, cartilage obtained from individuals diagnosed with osteoarthritis, post-traumatic osteoarthritis, rheumatoid arthritis, chondromatosis, costochondritis, relapsing polychondritis, herniation, chondrolysis, achondroplasia, chondrodysplasia, chondroma, chondrosarcoma, growth plate fracture and deformity, bone fracture, bone cyst, bone spur (osteophytes), bone tumor, osteosarcoma, craniosynostosis, fibrodysplasia ossificans progressive, myositis ossificans, progressive osseous heteroplasia, heterotopic ossification, vascular calcification/ossification, fibrous dysplasia, hypophosphatasia, metabolic bone disease, Paget's disease of bone, osteochondritis dissecans, osteogenesis imperfect, osteomalacia, osteopenia, osteoporosis, or osteopetrosis.

Osteogenic and/or chondrogenic progenitor cells may also be obtained from tissue that has undergone heterotopic ossification. As used herein, "heterotopic ossification" (HO) refers to the presence or development of bone in soft tissue where bone normally does not exist. In some cases, HO accompanies musculoskeletal trauma (e.g. osteoarthritis), spinal cord injury, central nervous system injury as well as atherosclerosis. In some embodiments, the cells are obtained from atherosclerotic tissue, plaques, or lesions.

Cartilage that is obtained from an individual diagnosed with a cartilage-related disease can then be enzymatically digested. Any enzyme capable of breaking down cartilage tissue matrix can be used in conjunction with the methods disclosed herein. These can include, without limitation, collagenases, pronases, hyaluronidases, proteases (such as matrix metalloproteases), and/or lipases. In one non-limiting embodiment, the procedure described in Example 1 of the invention details a procedure for isolating cartilage-derived progenitor cells obtained from diseased cartilage tissue from an individual diagnosed with osteoarthritis. In this embodiment, the cartilage tissue matrix is broken down using a combination of pronase and collagenase in order to obtain cells embedded in the cartilage tissue matrix.

Once the cartilage tissue matrix is broken down, cartilage-derived progenitor cells are enriched by differential adhesion to fibronectin. Fibronectin is a high-molecular weight (~440 kDa) glycoprotein of the extracellular matrix capable of binding to integrins. Similar to integrins, fibronectin also binds extracellular matrix components such as collagen, fibrin, and heparan sulfate proteoglycans (e.g. syndecans). Example 1 of the invention details a procedure for enriching cells obtained by enzymatic digestion of diseased cartilage via adhesion to fibronectin in culture. Fibronectin can be obtained from any number of commercially-available resources.

Cells that are enriched following adherence to fibronectin are then stabilized using an immortalization agent. Several methods exist for immortalizing mammalian cells in culture. One non-limiting method is to use viral genes, such as the simian virus 40 (SV40) T antigen, including functional fragments and variants of the same, including those compatible with human administration, to induce stabilization of cells in culture. SV40 T (large T) antigen has been shown to be an effective and reliable tool for the immortalization of many different cell types in culture. Further, the mechanism of stabilization by SV40 has been well documented. Without being bound to theory, it is believed that viral genes such as those provided by SV40 achieve immortalization by inactivating the tumor suppressor genes that can induce a senescent state in cells. Immortalization agents are widely available though commercial sources.

B. Methods for Treating Degenerative Cartilage and Bone Diseases

Cartilage tissue has a limited capacity for self-repair. There are several limitations on the ability of cartilage to repair itself in terms of restoring a long-term functional diarthrodial joint. At present, chondral repair tissue has an intermediate structure and composition between hyaline cartilage and fibrocartilage, rarely, if ever, replicating the actual structure of articular cartilage. There is disruption to the orientation and organization of the collagen fibrils, failure to make important interactions between macromolecules, in particular the proteoglycans and the collagen fibrillar network, thus resulting in a decrease in stiffness and in the ability to resist compressive loads. A major factor contributing to the low reparative capacities of articular cartilage is that the tissue is both avascular and aneural.

Treatments have been developed to try and overcome the problems that are faced when trying to treat articular cartilage defects caused by degenerative cartilage diseases. Potential treatments need to successfully integrate cells into a defect that will result in cartilage tissue having the same mechanical and structural properties as articular cartilage. Current cell based transplantation treatments involve the use of expanded autologous chondrocytes for transplantation into the defect to generate a repair tissue hopefully similar to that of the native articular cartilage. This cell based transplantation treatment is known as Autologous Chondrocyte Implantation (ACI) and was described by Brittberg et al. (1994, Osteoarthritis Cartilage. 2005 Feb.; 13(2):146-53) for the treatment of full-thickness cartilage defects. The problem with this technique is that it involves the extraction of healthy articular cartilage from a non-injured, non-weight bearing region of the joint. Contemporary research is looking into the use of mesenchymal stem cells (MSCs) as a cell source for use in tissue engineering and their infiltration into biodegradable scaffolds. Bone marrow derived MSCs have been focused on extensively but many other tissue types are now being considered as MSC sources such as cartilage and synovium.

Provided herein are methods for treating a degenerative cartilage or bone diseases in an individual in need thereof by administering cells from the stable chondroprogenitor cell lines derived using any of the methods disclosed herein. As will be discussed in more detail below, cell lines developed from the stable chondroprogenitor cells of the present invention possess characteristics of either chondroprogenitor or osteochondro-progenitor cells. As such, these cells may be used to treat both degenerative cartilage and bone diseases and injuries, respectively.

One of ordinary skill in the art may readily determine the appropriate concentration, or dose of the cartilage-derived progenitor cells disclosed herein for therapeutic administration. The ordinary artisan will recognize that a preferred dose is one that produces a therapeutic effect, such as preventing, treating and/or reducing inflammation associated with cartilage diseases, disorders and injuries, in a patient in need thereof. Of course, proper doses of the cells will require empirical determination at time of use based on several variables including but not limited to the severity and type of disease, injury, disorder or condition being treated; patient age, weight, sex, health; other medications and treatments being administered to the patient; and the like. An exemplary dose is in the range of about 0.25-2.0× $10^6$ cells. Other dose ranges include 0.1-10.0×$10^{6,7,8,9,10,11}$, or $10^{12}$ cells per dose or injection regimen.

An effective amount of cells may be administered in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of pharmaceutical composition. Where there is more than one administration of a pharmaceutical composition in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Cells derived from the methods of the present invention may be formulated for administration according to any of the methods disclosed herein in any conventional manner using one or more physiologically acceptable carriers optionally comprising excipients and auxiliaries. Proper formulation is dependent upon the route of administration chosen. The compositions may also be administered to the individual in one or more physiologically acceptable carriers. Carriers for cells may include, but are not limited to, solutions of normal saline, phosphate buffered saline (PBS), lactated Ringer's solution containing a mixture of salts in physiologic concentrations, or cell culture medium.

In further embodiments of the present invention, at least one additional agent may be combined with the cartilage-derived progenitor cells of the present invention for administration to an individual according to any of the methods disclosed herein. Such agents may act synergistically with the cells of the invention to enhance the therapeutic effect. Such agents include, but are not limited to, growth factors, cytokines, chemokines, antibodies, inhibitors, antibiotics, immunosuppressive agents, steroids, anti-fungals, anti-virals or other cell types (i.e. stem cells or stem-like cells, for example AMP cells), extracellular matrix components such as aggrecan, versican hyaluronic acid and other glycosaminoglycans, collagens, etc. Inactive agents include carriers, diluents, stabilizers, gelling agents, delivery vehicles, ECMs (natural and synthetic), scaffolds, and the like. When the cells of the present invention are administered conjointly with other pharmaceutically active agents, even less of the cells may be needed to be therapeutically effective.

The timing of administration of cell-based compositions will depend upon the type and severity of the cartilage disease, disorder, or injury being treated. In one embodiment, the cell-based compositions are administered as soon as possible after onset of symptoms, diagnosis or injury. In another embodiment, cell-based compositions are administered more than one time following onset of symptoms, diagnosis or injury. In certain embodiments, where surgery is required, the cell-based compositions are administered at surgery. In still other embodiments, the cell-based compositions are administered at as well as after surgery. Such post-surgical administration may take the form of a single administration or multiple administrations.

In some embodiments, the cells are administered parenterally to the individual. The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, epidural, intracerebral, intraosseous, intracartilagenous, and intrasternal injection or infusion.

Support matrices, scaffolds, membranes and the like into which the cell-based compositions can be incorporated or embedded include matrices which are recipient-compatible and which degrade into products which are not harmful to the recipient. Detailed information on suitable support matrices, etc. can be found in U.S. Pat. Nos. 8,058,066 and 8,088,732, both of which are incorporated herein by reference.

The methods disclosed herein can be used to treat any number of degenerative cartilage or bone diseases. Non-limiting examples of such diseases are described below.

Degenerative Disc Disease (DDD)—is a common musculoskeletal disorder that is the major cause of lower back pain. It includes the more severe degenerative conditions lumbar scoliosis, disc herniation and spinal stenosis. It involves sequential degenerative changes to the intervertebral disc (IVD), the chief support structure of vertebrates that confers tensile strength, stability and flexibility to the spine.

Chondrodystrophies—are a group of diseases characterized by disturbance of growth and subsequent ossification of cartilage. It is an object of the invention to treat and/or reduce the inflammation associated with these conditions.

Arthritis—Osteoarthritis occurs when the cartilage covering bones (called articular cartilage) is thin and eventually completely wears out, resulting in a "bone against bone" joint, reduction in motion, and pain. Osteoarthritis primarily affects the joints exposed to high stress and is therefore generally considered the result of "wear and tear". It is often treated by arthroplasty, which is the replacement of the joint with a synthetic joint. In some embodiments, the methods of the present invention can be used to prevent, treat and/or reduce the inflammation associated with osteoarthritis. Rheumatoid arthritis is a chronic inflammatory disorder that typically affects the small joints in the hands and feet. Unlike the damage seen in osteoarthritis, rheumatoid arthritis affects the lining of the joints, causing a painful swelling that can eventually result in bone erosion and joint deformity. Rheumatoid arthritis is an autoimmune disorder that occurs when the immune system attacks the body's own tissues. In addition to causing joint problems, rheumatoid arthritis sometimes can affect other organs of the body, such as the skin, eyes, lungs and blood vessels. Gouty arthritis is a type of arthritis that occurs when uric acid builds up in blood and causes inflammation in the joints. Acute gout is a painful condition that often affects only one joint. Chronic gout is repeated episodes of pain and inflammation. More than one joint may be affected. Psoriatic arthritis is a type of arthritic inflammation that occurs in about 15 percent of patients who have a skin rash called psoriasis. This particular arthritis can affect any joint in the body, and symptoms vary from person to person. Research has shown that persistent inflammation from psoriatic arthritis can lead to joint damage.

Traumatic rupture or detachment—The cartilage in joints, especially the knee, is frequently damaged and suffers traumatic rupture or detachment. This can be partially repaired through knee cartilage replacement therapy. In some embodiments, the methods of the present invention can be used to treat and/or reduce the inflammation associated with traumatic rupture or detachment of cartilage.

Achondroplasty—Reduced proliferation of chondrocytes in the epiphyseal plate of long bones during infancy and childhood, resulting in dwarfism. In some embodiments, the methods of the present invention can be used to treat epiphyseal plate chondrocytes such that there is an increased proliferation of cells which will form normal amounts of cartilage.

Costochondritis—Inflammation of the costal cartilage in the ribs, which causes chest pain. In some embodiments, the methods of the present invention can be used to treat and/or reduce the inflammation associated with costochondritis.

Intervertebral disc herniation—Asymmetrical compression of an intervertebral disc ruptures the sac-like disc, causing a herniation of its soft content. The hernia often compresses the adjacent nerves and causes back pain. In some embodiments, the methods of the present invention can be used to treat and/or reduce the inflammation associated with intervertebral disc herniation.

Relapsing polychondritis destruction—This disease is believed to be an autoimmune disease affecting cartilage, especially of the nose and ears, causing disfiguration. In severe cases, death can occur by suffocation as the larynx loses its rigidity and collapses. In some embodiments, the methods of the present invention can be used to treat and/or reduce the inflammation associated with relapsing polychondritis destruction.

Ankylosing spondylitis, or AS, is a fairly rare form of arthritis that primarily affects the spine, although other joints can become involved. It causes inflammation of the spinal joints (vertebrae) that can lead to severe, chronic pain and discomfort. In the most advanced cases, this inflammation can lead to new bone formation on the spine, causing the spine to fuse in a fixed, immobile position, sometimes creating a forward-stooped posture. This forward curvature of the spine is called kyphosis. In some embodiments, the methods of the present invention can be used to treat and/or reduce the inflammation associated with ankylosing spondylitis.

Other degenerative cartilage tissue diseases capable of being treated with the methods and cells of the present invention (such as chondroprogenitor cells) include, without limitation, osteoarthrosis, degenerative diseases of the joints, collagen deficiencies, cartilage or bone diseases characterized by endochondrial ossifications, rheumatoid arthritis, juvenile arthritis, undifferentiated chronic arthritis, polyarthritis, secondary arthritis of autoimmune origin, systemic lupus erythematosus arthritis, psoriasic arthritis, Crohn's disease arthritis, arthritis of dysmetabolic origin, monosodium urate arthropathy, pyrophosphate arthropathy, calcium oxalate arthropathy, infectious arthritis, arthritis due to osteoporosis, aseptic osteonecrosis, and benign and malignant bone tumors.

In other embodiments, degenerative bone tissue diseases capable of being treated with the methods and cells of the present invention (such as osteochondro-progenitor cells) include, without limitation, fracture, osteoporosis, osteopenia, Paget's disease, malignant bone disease, bone degeneration due to hyperparathyroidism, and other conditions associated with increased bone resorption or turnover.

C. Screening for Compounds to Inhibit Osteophyte Formation and/or Promote Cartilage Joint Repair In some embodiments, also provided herein are methods for identifying a candidate therapeutic molecule (i.e. a compound) capable of inhibiting osteophyte formation and/or promote cartilage joint repair. The methods utilize any of the stable cartilage-derived progenitor cell lines disclosed herein. In some embodiments, the cells of the present invention are contacted directly with the candidate therapeutic molecule in culture and the effects of the same are assessed on cellular phenotype using any commonly used in vitro assessment technique known in the art. In some instances, the desired cellular phenotype is, for example, inhibition of osteophyte (i.e. bone spur) formation, inhibition of chondrocyte dedifferentiation, inhibition of chondrocyte hypertrophy as well as promotion of chondrogenesis. Candidate compounds can be, without limitation, small molecule chemical compounds, antibodies, proteins, inhibitory nucleic acids, or any combination thereof.

In some aspects, the candidate compound is a small molecule. Small molecules are preferably organic molecules other than binding polypeptides or antibodies as defined herein. Organic small molecules may be identified and chemically synthesized using known methodology (see, e.g., PCT Application Publication Nos. WO 00/00823 and WO 00/39585, the disclosures of which are incorporated by reference herein). Organic small molecules are usually less than about 2000 Daltons in size, alternatively less than about 1500, 750, 500, 250 or 200 Daltons in size, wherein such organic small molecules that are capable of binding to a polypeptide as described herein may be identified without undue experimentation using well known techniques. In this regard, it is noted that techniques for screening organic small molecule libraries for molecules that are capable of binding to a polypeptide target are well known in the art (see, e.g., PCT Application Publication Nos. WO 00/00823 and WO 00/39585.

In some aspects, the small molecule chemical compound is a component of a combinatorial chemical library. Combinatorial chemical libraries are a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as carbohydrates, oligonucleotides, and small organic molecules, etc. Such libraries have a variety of uses, such as immobilization and chromatographic separation of chemical compounds, as well as uses for identifying and characterizing ligands capable of binding a target molecule or mediating a biological activity of interest.

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports. To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. In some embodiments, the small molecules are less than about 2000 Daltons in size, alternatively less than about 1500, 750, 500, 250 or 200 Daltons in size.

References disclosing the synthesis of chemical libraries as well as the deconvolution of the individual compounds of those libraries onto individual solid phase supports, can be found in U.S. Patent Application No. 2009/0032592; Needels et al., (1993), Proc. Natl. Acad. Sci. USA 90: 10700-10704; and PCT Application Publication No. WO 97/15390, the disclosures of which are incorporated by reference herein.

III. Compositions of the Invention

The present invention encompasses cartilage-derived progenitor cell lines derived from individuals diagnosed with a cartilaginous disease or lesion. The table below lists the claimed cell line designations and their corresponding deposit dates.

| Cell line Designation | ATCC Deposit Designation | ATCC Deposit Date |
|---|---|---|
| CPCL1 | | 28 Feb. 2017 |
| CPCL14 | | 28 Feb. 2017 |
| NCPCL3 | | 28 Feb. 2017 |

The cell lines were deposited and will be made available to the public without restriction, but subject to patent rights, with the American Type Culture Collection (ATCC), 10801 University Boulevard, Manassas, Va., 20110. The claimed cell lines were deposited on behalf Rhode Island Hospital. These deposits were made and will be maintained in accordance with, and under the terms of, the Budapest Treaty with respect to cell line deposits for the purposes of patent procedure. These deposits will be maintained without restriction at the ATCC depository, which is a public depository, for a period of 30 years, or five years after the most recent request, or for the effective life of the patent, whichever is longer, and will be replaced if they become nonviable during that period.

A. Cartilage-Derived Progenitor Cells from Individuals with Osteoarthritis

Provided herein are stable cartilage-derived progenitor cell lines obtained via any of the methods disclosed herein from individuals with osteoarthritis. Each of the cell lines posses a distinct and unique gene expression profile which differentiates them from other connective tissue progenitor cells. Gene expression can be measured by any means known in the art and can include, without limitation, measurements of mRNA expression (such as, RT-PCR, Northern Blot, run-on assays, microarray, or in situ hybridization) or protein expression (such as Western Blot or any other antibody-based assay, two dimensional gel electrophoresis, radio immunoassay, ELISA, etc.).

In some embodiments, the stable cartilage-derived progenitor cell lines of the present invention derived from individuals with osteoarthritis express less aggrecan (ACAN; Gen Bank Accession Nos. NM_001135.3 and NP_001126), type II collagen (COL2A1; Gen Bank Accession Nos. NM_001844 and NP_001835), SOX9 (Gen Bank Accession Nos. NM_000346 and NP_000337), matrilin-3 (MATN3; Gen Bank Accession Nos. NM_002381 and NP_002372), and/or lubricin (PRG4; Gen Bank Accession Nos. NM_001127708 and NP_001121180) relative to chondrocytes derived from healthy adult tissue, such as any of about 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 or 20 times less ACAN, COL2A1, SOX9, MATN3, and/or PRG4 relative to chondrocytes derived from healthy adult tissue. In further embodiments, the stable cartilage-derived progenitor cell lines of the present invention express any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 72%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% less ACAN, COL2A1, SOX9, MATN3, and/or PRG4 relative to chondrocytes derived from healthy adult tissue.

In yet other embodiments, the stabilized cells express comparable levels of SOX9, MATN3, and/or PRG4 relative to bone marrow-derived mesenchymal stein cells (BM-MSCs). As used herein, when two cell types "express comparable levels" of a particular gene or protein product, it means that the expression of the particular gene differs by less than about 10%, 9%, 8%, 7%, 6%, 5%, 4%, 3%, 2%, or 1%, between the two cell types.

In further embodiments, the stabilized cartilage-derived progenitor cells of the present invention express less type I collagen (COL1; Gen Bank Accession No. NM_000088; UniProt Accession No. P02452) relative to BM-MSCs, such as any of about 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 or 20 times less COL1 relative to BM-MSCs. In further embodiments, the stable cartilage-derived progenitor cell lines of the present invention express any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 72%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, less COL1 relative to BM-MSCs.

Mesenchymal stem cells (MSCs) are multipotent cells that have a fibroblast-like morphology, express a specific set of surface antigens, and are capable of differentiating into adipocytes, chondrocytes, and osteocytes. In certain embodiments, the stabilized cartilage-derived progenitor cells of the present invention express one or more mesenchymal cell surface markers including, without limitation, of CD29 (Gen Bank Accession Nos. NM_002211 and NP_002202), CD49c (Gen Bank Accession Nos. NM_002204 and NP_002195), CD105 (Gen Bank Accession Nos. NM_000118 and NP_000109), and/or CD166 (Gen Bank Accession Nos. NM_001243280 and NP_001230209). On the other hand, in some embodiments the stabilized cartilage-derived progenitor cells of the present invention do not express the BM-MSC cell surface marker SSEA4.

Chondrocytes are the only cells found in healthy cartilage. These cells produce and maintain the cartilaginous matrix, which consists mainly of collagen and proteoglycans. In some embodiments, the stabilized cartilage-derived progenitor cells of the present invention express one or more chondrocyte cell surface markers including, without limitation CD54 (Gen Bank Accession Nos. NM_000201 and NP_000192). However, in other embodiments, the cells of the present invention do not express the chondrocyte cell surface marker CD106 (Gen Bank Accession Nos. NM_001078 and NP_001069).

Moreover, cell lines derived from the stabilized cartilage-derived progenitor cells of the present invention can possess properties associated with either chondroprogenitor cells, which are prone to chondrogenesis (cartilage formation) or osteochondro-progenitor cells, which are prone for osteogenesis (bone formation). In some embodiments, cell lines derived from the stabilized cartilage-derived progenitor cells of the present invention exhibit limited to no response to induction with adipogenic medium (evidenced by, for example staining with Oil Red O dye).

1. Osteochondro-Progenitor Cells

Cell lines derived from stabilized cartilage-derived progenitor cells which have properties associated with osteogenesis are a potential source of osteophytes. Commonly referred to as bone spurs, osteophytes are bony projections that form along joint margins. Osteophyte formation has been classically related to any sequential and consequential changes in bone formation that is due to aging, degeneration, mechanical instability, and disease. Often osteophytes form in osteoarthritic joints as a result of damage and wear from inflammation. Calcification and new bone formation can also occur in response to mechanical damage in joints. Accordingly, cell lines possessing these properties have the potential to be of great value for drug screening to inhibit osteophyte formation and/or promote cartilage joint repair. In addition, these stem cell lines can also be used for tissue engineering purposes such as bone tissue formation.

In some embodiments, cell lines derived from the stabilized cartilage-derived progenitor cells of the present invention that possess properties associated with osteochondro-progenitor cells express more transcription factor PRX1 (Gen Bank Accession Nos. NM_006902 and NP_008833), alkaline phosphatase (ALPL; Gen Bank Accession Nos. NM_000478 and NP_000469), and/or the mesenchymal cell surface marker CD90 (Gen Bank Accession Nos. NM_001311160 and NP_001298089) relative to cartilage-derived progenitor cells of the present invention that possess properties associated with chondroprogenitor cells, such as expression of any of about 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 or 20 times greater amounts of transcription factor PRX1, ALPL, and/or CD90. In further embodiments, cell lines derived from the stabilized cartilage-derived progenitor cells of the present invention that possess properties associated with osteochondro-progenitor cells express any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 72%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% more transcription factor PRX1, ALPL and/or CD90 relative to cartilage-derived progenitor cells of the present invention that possess properties associated with chondroprogenitor cells.

Cell lines derived from the stabilized cartilage-derived progenitor cells of the present invention can be made to undergo differentiation towards an osteogenetic phenotype by culturing them in differentiation medium, several of which are available commercially (e.g., Stempro® Osteogenesis differentiation Media (Life Technologies, Grand Island, N.Y.). As such, in these embodiments, cell lines derived from the stabilized cartilage-derived progenitor cells of the present invention that possess properties associated with osteochondro-progenitor cells exhibit a more robust response to osteogenic differentiation medium evidenced by staining with Alizarin Red, such as any of about 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 or 20 times more robust response to osteogenic differentiation medium relative to cartilage-derived progenitor cells of the present invention that possess properties associated with chondroprogenitor cells. In further embodiments, cell lines derived from the stabilized cartilage-derived progenitor cells of the present invention that possess properties associated with osteochondro-progenitor cells exhibit any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 72%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% greater response to osteogenic differentiation medium (as evidenced by, for example, Alizarin Red staining) relative to cartilage-derived progenitor cells of the present invention that possess properties associated with chondroprogenitor cells.

2. Chondroprogenitor Cells

Chondroprogenitor cells are intermediate in development between MSCs and terminally differentiated chondrocytes. Cell lines derived from the stabilized cartilage-derived progenitor cells of the present invention can be made to undergo differentiation towards a chondrogenic phenotype by culturing them in differentiation medium, several of which are available commercially (e.g., Stempro® Chondrocyte Differentiation Media (Life Technologies, Grand Island, N.Y.). Consequently, in these embodiments, cell lines derived from the stabilized cartilage-derived progenitor cells of the present invention that possess properties associated with chondroprogenitor cells exhibit a more robust response to chondrocyte differentiation media evidenced by staining with Safranin-O, such as any of about 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 or 20 times more robust response to chondrocyte differentiation medium relative to cartilage-derived progenitor cells of the present invention that possess properties associated with osteochondro-progenitor cells.

In further embodiments, cell lines derived from the stabilized cartilage-derived progenitor cells of the present invention that possess properties associated with chondroprogenitor cells exhibit any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 72%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% greater response to chondrocyte differentiation medium (as evidenced by, for example, Safranin-O staining) relative to cartilage-derived progenitor cells of the present invention that possess properties associated with osteochondro-progenitor cells.

In other embodiments, cell lines derived from the stabilized cartilage-derived progenitor cells of the present invention that possess properties associated with chondroprogenitor cells express one or more long non-coding RNAs (lncRNAs) selected from FAM86, 10324 and TVAS5 compared to cartilage-derived progenitor cells of the present invention that possess properties associated with osteochondro-progenitor cells and which do not express one or more lncRNAs.

B. Cartilage-Derived Progenitor Cells from Individuals with Osteosarcoma

Also provided herein are stable cartilage-derived progenitor cell lines obtained via any of the methods disclosed herein from individuals with osteosarcoma. As described in Example 8, chondroprogenitor cell lines can also be derived from normal cartilage tissue obtained from individuals with osteosarcoma in accordance with the methods disclosed herein.

In some embodiments, stabilized cartilage-derived progenitor cells of the present invention obtained from the cartilage of individuals with osteosarcoma exhibit any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 72%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% higher expression of ACAN versus expression of ACAN in BM-MSCs.

In further embodiments, stabilized cartilage-derived progenitor cells of the present invention obtained from the cartilage of individuals with osteosarcoma exhibit any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 72%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% decreased expression of PRX and/or Type X collagen versus expression of PRX and/or Type X collagen in BM-MSCs.

In additional embodiments, stabilized cartilage-derived progenitor cells of the present invention obtained from the cartilage of individuals with osteosarcoma exhibit any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 72%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% decreased expression of SOX9, ACAN, PRX and/or Type X collagen versus expression of SOX9, ACAN, PRX and/or Type X collagen in mature chondrocytes from healthy adult tissue.

In still further embodiments, stabilized cartilage-derived progenitor cells of the present invention obtained from the cartilage of individuals with osteosarcoma exhibit any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 72%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% higher expression of collagen I versus expression of collagen I in mature chondrocytes from healthy adult tissue.

The stabilized cartilage-derived progenitor cells of the present invention obtained from the cartilage of individuals with osteosarcoma describe above include progenitor cells from any of the nCPCL 2, nCPCL 3, nCPCL 4, nCPCL A1, nCPCL 3C, nCPCL 5E, nCPCL 6B and/or nCPCL 6F cell lines. A discussed in Examples 9 and 10, cells derived from these cells lines can be characterized as CD90–/CD105+/CD166+ and exhibit adherence to the inner meniscus in an in vitro model of soft tissue repair. By four weeks, the cells enter the inner avascular region of the meniscus, integrating into the tissue and enhancing proteoglycan content by any of 10%, 20%, 30%, 40%, 50%, 60%, 70%, 80%, 90%, or 100%, inclusive of values falling in between these percentages. Further, these cartilage-derived progenitors can migrate to areas of injuries in the meniscus.

IV. Kits

In addition, the present invention includes kits for culturing any of the stabilized cartilage-derived progenitor cells of the present invention in accordance with any of the methods disclosed herein. In addition to the cell lines described herein, the kits can contain one or more of a mammalian cell culture base medium and/or a mammalian cell culture feed medium. The kit can also include written instructions for using the kit, such as instructions for using the any of the cells or cell lines disclosed herein for screening for candidate compounds capable of inhibition of osteophyte formation and/or promotion of chondrogenesis.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The invention can be further understood by reference to the following examples, which are provided by way of illustration and are not meant to be limiting.

EXAMPLES

Example 1: Isolation, Enrichment and Stabilization of Cartilage-Derived Progenitors This Example describes the generation of stable cartilage-derived progenitor cells from diseased articular cartilage.

Materials and Methods

Cells were isolated from the partial or full thickness of human articular cartilage obtained from individuals undergoing surgical procedures related to osteoarthritis. Cartilage tissue samples were kept at 4° C. and rushed within 2 hours post-surgery from the operating room (OR) to the laboratory for processing.

Samples were washed three times with 1×HBSS and the full depth of articular cartilage (from the articular surface to the deep zone) was diced into small fragments. The diced cartilage tissue was treated with 5.0 mL of Pronase (Roche, Indianapolis, Ind., USA) in 1×HBSS at a concentration of 2.0 mg/mL for 30 minutes in a 37° C. shaking water bath. The digestion solution was then decanted and the cartilage fragments were washed twice with DMEM. Cartilage fragments were then further digested in 10 mL of Type IA Crude Bacterial Collagenase (Sigma-Aldrich, St. Louis, Mo., USA) at a concentration of 1.0 mg/mL for 8 hrs in a 37° C. shaking water bath. Cells were strained through a 100 µm nylon cell strainer (BD, Franklin Lakes, N.J., USA) to remove clumps and washed three times with 5.0 mL of DMEM supplemented with 10% FBS. Cells were then counted using a hemacytometer. Cartilage-derived chondroprogenitor cells were enriched using a slightly modified version of a previously described method of differential cell adhesion using fibronetin (Williams et al. *PLoS One* 2010; 5:e13246) (FIG. 1).

Dulbecco's Modified Eagle Medium (DMEM), fetal bovine serum (FBS), Hank's Balanced Salt Solution (HBSS) and Penicillin Streptomycin (Pen Strep) were purchased from Life Technologies, Grand Island, N.Y. Chondrocytes were grown using DMEM supplemented with 10% FBS and 1% Pen Strep. CPCs were maintained in DMEM supplemented with 10% FBS, 1% Pen Strep, 100 mM HEPES, 2 mM L-glutamine, 0.1 mM ascorbic acid, 0.1 mM sodium pyruvate, 0.5 mg/mL L-glucose (DMEM+). All cells were grown in a 37° C. cell culture incubator. Cells were then counted using a hemacytometer. CPCs were enriched using a slightly modified version of a previously described method of differential cell adhesion using fibronetin (Williams et al., *PLoS One* 2010; 5:e13246). Cells (2000 cells/mL) were plated in 60 mm dishes that had been coated at 4° C. overnight with 10 µg/mL of fibronectin in 0.1 M PBS containing 1.0 mM MgCl and 1.0 mM $CaCl_2$. Cells were seeded and left for 20 min at 37° C. After 20 min, non-adherent cells were removed from the plates and fresh DMEM+ was added. Adherent cells were observed and counted under a light microscope.

Results

Approximately after 2 weeks, single cells that had formed individual colonies consisting of ≥32 cells were isolated using glass cloning cylinders (Sigma-Aldrich, St. Louis, Mo., USA), taking care not to cross contaminate with cells from neighboring regions, and reseeded in individual wells of 6-well cell culture plates (FIG. 1). Colonies were cultured for one week. After one week of culture, these cartilage-derived progenitor cell colonies were stabilized using the retroviral vector pRetro-E2 SV40 (Applied Biological Materials Inc., Richmond, BC, Canada) according to the manufacturer's instructions. Generated cell lines were expanded and subsequent experiments to characterize specific cell lines were conducted.

Example 2: Gene Expression Analysis of Cartilage-Derived Progenitor Cell Lines

This example describes gene expression in cartilage-derived progenitor cells obtained from diseased cartilage tissue. Each cartilage-derived chondroprogenitor cell line that was generated was first characterized using gene expression analysis of endogenous type II collagen (COL2A1), aggrecan (ACAN) and fibronectin receptor (CD49e) messenger RNA (mRNA) levels. Subsequently, selected groups were further analyzed for the expression of transcription factors PRX1 and SOX-9 as well as cartilage extracellular protein matrilin-3 (MATN3) and the cartilage surface lubricating protein lubricin (PRG4)

Materials and Methods

Gene expression analysis was conducted using real-time PCR. Total mRNA was isolated from cells using an RNAqueous Kit (Ambion, Austin, Tex., USA) according to manufacturer's instructions. mRNA was reverse transcribed using iScript cDNA Synthesis Kit (Bio-Rad, Hercules, Calif., USA) according to the manufacturer's instructions. Table 1 lists all forward and reverse primer sequences used to conduct gene expression analysis in this study. Ribosomal RNA (rRNA) 18S was used as the housekeeping gene for normalization. mRNA transcript levels were calculated using the delta delta Ct (ΔΔCt) method, normalized to rRNA 18S expression as follows: X=2-ΔΔCt, in which ΔΔCt= (CtExp−Ctl8S)−(CtCtl−Ctl8S) and X=Relative transcript; CtCtl=Ct of control group. Statistics were done using one-way analysis of variance (ANOVA) followed by post-hoc analysis. Error bars represent one standard deviation of the mean.

Statistics were performed using either one-way analysis of variance (ANOVA) followed by post-hoc analysis or a two-tailed Student's t-test. All quantitative analyses were conducted using sample sizes of 3 or greater. Error bars represent±one standard deviation of the mean. P-values smaller or equal to 0.05 were considered statistically significant.

TABLE 1

Forward and reverse sequences of primers used to conduct Real-time RT-PCR for gene mRNA expression analysis

| Human gene | Forward Seq. | Reverse Seq. |
|---|---|---|
| ACAN | 5'-ACCAGACGGGCCTCCCAGAC-3' (SEQ ID NO: 1) | 5'-ACAGCAGCCACACCAGGAAC-3' (SEQ ID NO: 2) |
| COL2A1 | 5'-TGAGGGCGCGGTAGAGACCC-3' (SEQ ID NO: 3) | 5'-TGCACACAGCTGCCAGCCTC-3' (SEQ ID NO: 4) |
| CD49e | 5'-GGCTTCAACTTAGACGCGGA-3' (SEQ ID NO: 5) | 5'-ATTCAATGGGGGTGCACTGT-3' (SEQ ID NO: 6) |
| SOX9 | 5'-GGACCAGTACCCGCACTTGCA-3' (SEQ ID NO: 7) | 5'-GTTCTTCACCGACTTCCTCCGCCG-3' (SEQ ID NO: 8) |
| MATN3 | 5'-TGAGGGCTACACTCTGAATGC-3' (SEQ ID NO: 9) | 5'-GTGCTTCCTCAGTGGCTGAA-3' (SEQ ID NO: 10) |
| PRG4 | 5'-TTCATCTCAAGAGCTTTCCTGT-3' (SEQ ID NO: 11) | 5'-TGATGGTTTGAGATGCTCCTG-3' (SEQ ID NO: 12) |
| LPL | 5'-GACACTTGCCACCTCATTCC-3' (SEQ ID NO: 13) | 5'-AGCCATGGATCACCATGAAGG-3' (SEQ ID NO: 14) |
| FABP4 | 5'-TGGAAACTTGTCTCCAGTGAA-3' (SEQ ID NO: 15) | 5'-TCACATCCCCATTCACACTGA-3' (SEQ ID NO: 16) |
| BGLAP | 5'-CTGGCCGCACTTTGCATCGCTG-3' (SEQ ID NO: 17) | 5'-AGCCAACTCGTCACAGTCCGGA-3' (SEQ ID NO: 18) |
| PPARG | 5'-CGTGGCCGCAGAAATGAC-3' (SEQ ID NO: 19) | 5'-AGGAGTGGGAGTGGTCTTCC-3' (SEQ ID NO: 20) |
| ALPL | 5'-CTGGACGGACCCTCGCCAGTG-3' (SEQ ID NO: 21) | 5'-TGCAATCGACGTGGGTGGGAGG-3' (SEQ ID NO: 22) |
| PRX1 | 5'-CATCGTACCTCGTCCTGCTC-3' (SEQ ID NO: 23) | 5'-GTAAACAACATCTTGGGAGGGA-3' (SEQ ID NO: 24) |

Results

Nine stable CPC lines were generated. Each cell line was characterized using gene expression analysis of endogenous aggrecan (ACAN), COL2A1, and CD49e mRNA levels. Relative to adult human articular chondrocytes, human cartilage-derived progenitor cell lines exhibit lower mRNA expression of chondrogenic markers ACAN and COL2A1 (FIG. 2B, FIG. 2C). This indicated that, like primary CPCs, these generated CPC lines have preserved molecular characteristics of low chondrogenic marker expression. Furthermore, a pattern emerged where all cell lines could be divided into two groups based on the expression levels of chondrogenic markers ACAN and COL2A1. It was possible to divide the tested lines into two distinguishable groups (Group 1 and Group 2) based on their relative chondrogenic marker expression levels. Group I (GI) consisting of CPC lines 1, 2 and 5, expressed higher levels of chondrogenic markers, while Group II (GII) consisting of lines 6, 8, 12, 13, 14 and 18, expressed lower levels of chondrogenic markers. (FIG. 2B, FIG. 2C). Interestingly, GI contained the cell lines that were derived from individual cells with higher CFE while GII contained the lines derived from those of lower CFE. Higher relative fibronectin receptor (CD49e) mRNA expression levels was also observed in all but two of the lines that constituted Group 2, relative to lines in Group 1 (FIG. 2D). This observation indicated that most of the lines that express lower chondrogenic marker expression levels also express higher levels of CD49e. This result was consistent with the observation that primary CPCs expressed higher levels of CD49e mRNA than PHCs (FIG. 2A), and suggested that the CPCs of lower CFE were the main contributors of high CD49e mRNA levels in primary CPCs. Taken together, these results indicate that these cartilage derived progenitors are divided into at least two distinguishable subsets based on their expression of the aforementioned chondrogenic makers and their expression of the fibronectin receptor.

A representative line was selected from each group (CPCL2, from Group 1; CPCL18, from Group 2) to conduct further comparative gene expression analysis. The mRNA expression levels of transcription factor PRX1, transcription factor SOX9, matrilin-3 (MATN3), type I collagen (COL1) and lubricin (PRG4) were profiled in each of these cartilage-derived progenitor cell lines, relative to mature human chondrocytes (PHCs) and bone marrow-derived mesenchymal stem cells (BM-MSCs) (FIG. 3). CPCL2 and 18 could be distinguished from one another based on their PRX1 expression profiles. Relative to CPCL2, CPCL18 exhibited a 3-fold increase in PRX1 expression level (FIG. 3A). Furthermore, PRX1 expression level in CPCL18 was approximately 1.7-fold of that observed in mature chondrocytes (FIG. 3A). SOX9, MATN3 and PRG4 expression levels in both progenitor lines were comparable to that of BM-MSCs, but they were significantly lower than that of articular chondrocytes (FIG. 3B, FIG. 3C, FIG. 3E). PRG4 has been proposed as a marker of CPCs. However, PRG4 expression levels in both CPC lines were significantly lower than PHCs and comparable to that of BM-MSCs (FIG. 3E). However, COL1 expression in both progenitor lines were significantly lower than that of BM-MSCs (FIG. 3D). These results indicate that CPCL2 and 18 are distinguished from one another by their PRX1 expression profiles. SOX-9, MATN3 and PRG4 expression profiles may be used to distinguish both progenitor lines from mature chondrocytes. Similarly, their COL1 expression profiles may be used to distinguish both progenitor lines from BM-MSCs.

Despite the differences of mRNA expression patterns between the CPC lines in GI and GII, the cellular morphologies of these cell lines were similar to one another between the two groups (FIG. 7). While bone marrow derived MSCs (BM-MSCs) presented a long tubular structure and articular chondrocytes were consistently shorter, the morphologies of the CPC lines were between these two types of cells. Furthermore, the morphology of CPC lines reflected that of primary CPCs as observed by us as well as by others (Williams et al., PLoS One 2010; 5:e13246; Seol et al., Arthritis Rheum 2012; 64:3626-37). To determine whether the differences of CPC lines between GI and GII were due to individual patient variation, the individual patient origin of each cell line was determined by genetic profiling including multiple autosomal short tandem repeat (STR) loci and the gender identity locus amelogenin (Table 2). The STR profiles indicated that lines 1, 2, 5, 6, 12 and 18 originated from the same patient (female), whereas lines 8, 13 and 14 originated from a different patient (male). Because CPCs in the same group were from different OA patients (e.g., GII contained lines 6, 12, 18 from one patient and lines 8, 13, 14 from another patient), the differences between lines in GI and MI cannot be attributed to individual patient variation.

Table 2: Each cell line was profiled in order to determine their patient origin using autosomal short tandem repeat (STR) loci and the amelogenin locus. Profile results confirmed that cell lines 1, 2, 5, 6, 12 and 18 originated from an individual female patient. Cell lines 8, 13 and 14 originated from an individual male patient. CPCL1 appears to have an allele difference in D18S51 locus compared to the rest of the lines from the same patient. This difference is likely due to genetic instability common in transformed cells.

Example 3: Cell Surface Marker Analysis of Cartilage-Derived Progenitor Cell Lines This Example shows cell surface marker analysis of cartilage-derived progenitors was conducted using Fluorescently Activated Cell Sorting (FACS). Chondrocytes, BM-MSCs, CPCL2 and CPCL18 were tested for the following cell surface markers: CD49c, CD54, CD90 and CD166.

Materials and Methods

Pre-conjugated antibodies CD49c-APC and CD166-PE were purchased from BioLegend, San Diego, Calif., USA. SSEA4-PE, CD29-APC, CD54-PE, CD90-FITC, CD105-APC, CD106-APC were purchased from Miltenyi Biotec Inc., San Diego, Calif., USA. Isotype IgG control antibodies were also purchased from Miltenyi Biotec Inc. Cells to be stained were washed 2 times with 5.0 mL of sterile HBSS and detached using 2.0 mL of TrypLE Express (Life Technologies, Grand Island, N.Y., USA). Cells were washed with DMEM supplemented with 10% FBS and spun down using a centrifuge set for 300×g. Cells were washed once again with 5.0 mL sterile 1×PBS and spun down at 300×g. Viable cell number was quantified using a hemacytometer and 0.4% Trypan blue solution (Life Technologies, Grand Island, N.Y., USA). For each sample to be stained, 1.0×106 viable cells were resuspended in 100 µL of Flow buffer (1x PBS, pH 7.2, 0.5% bovine serum albumin and 2 mM EDTA). Pre-conjugated antibody (10 µL) was added to the resuspension, mixed and incubated for 10 min in the dark at 4° C. Cells were washed 3 times with 1.0 mL of 1×PBS and resuspended in 500 mL of Flow buffer before single channel FACS analysis using an Accuri C6 Flow Cytometer (BD Biosciences, San Jose, Calif., USA). Control experiments for non-specific staining using mouse IgG were performed alongside all experiments.

Statistics were performed using either one-way analysis of variance (ANOVA) followed by post-hoc analysis. All quantitative analyses were conducted using sample sizes of

TABLE 2

Each cell line was profiled in order to determine their patient origin using autosomal short tandem repeat (STR) loci and the amelogenin locus. Profile results confirmed that cell lines 1, 2, 5, 6, 12 and 18 originated from an individual female patient. Cell lines 8, 13 and 14 originated from an individual male patient. CPCL1 appears to have an allele difference in D18S51 locus compared to the rest of the lines from the same patient. This difference is likely due to genetic instability common in transfonned cells.

| Line | D3S1358 | D21S11 | D18S51 | Penta E | D5S818 | D13S317 | D7S820 | D16S539 | CSF1PO |
|---|---|---|---|---|---|---|---|---|---|
| CPCL1 | 16 | 29 | 13, 21, 22 | 12 | 9, 11 | 9, 11 | 8, 10 | 11 | 10, 11 |
| CPCL2 | 16 | 29 | 13, 21 | 12 | 9, 11 | 9, 11 | 8, 10 | 11 | 10, 11 |
| CPCL5 | 16 | 29 | 13, 21 | 12 | 9, 11 | 9, 11 | 8, 10 | 11 | 10, 11 |
| CPCL6 | 16 | 29 | 13, 21 | 12 | 9, 11 | 9, 11 | 8, 10 | 11 | 10, 11 |
| CPCL8 | 16, 18 | 28, 32.2 | 19 | 10, 14 | 11 | 9, 12 | 8, 11, 11.1 | 10, 12 | 12, 13 |
| CPCL12 | 16 | 29 | 13, 21 | 12 | 9, 11 | 9, 11 | 8, 10 | 11 | 10, 11 |
| CPCL13 | 16, 18 | 28, 32.2 | 13, 21 | 10, 14 | 11 | 9, 12 | 8, 11, 11.1 | 10, 12 | 12, 13 |
| CPCL14 | 16, 18 | 28, 32.2 | 19 | 10, 14 | 11 | 9, 12 | 8, 11, 11.1 | 10, 12 | 12, 13 |
| CPCL18 | 16 | 29 | 13, 21 | 12 | 9, 11 | 9, 11 | 8, 10 | 11 | 10, 11 |

| Line | Penta D | vWA | D8S1179 | TPOX | FGA | AMEL |
|---|---|---|---|---|---|---|
| CPCL1 | 9, 11 | 14, 19 | 12, 14 | 8, 12 | 20, 21 | X |
| CPCL2 | 9, 11 | 14, 19 | 12, 14 | 8, 12 | 20, 21 | X |
| CPCL5 | 9, 11 | 14, 19 | 12, 14 | 8, 12 | 20, 21 | X |
| CPCL6 | 9, 11 | 14, 19 | 12, 14 | 8, 12 | 20, 21 | X |
| CPCL 8 | 11, 12 | 17, 19 | 8, 14 | 8, 10 | 19, 21 | X, Y |
| CPCL12 | 9, 11 | 14, 19 | 12, 14 | 8, 12 | 20, 21 | X |
| CPCL13 | 11, 12 | 17, 19 | 8, 14 | 8, 10 | 19, 21 | X, Y |
| CPCL14 | 11, 12 | 17, 19 | 8, 14 | 8, 10 | 19, 21 | X, Y |
| CPCL18 | 9, 11 | 14, 19 | 12, 14 | 8, 12 | 20, 21 | X |

3 or greater. Error bars represent±one standard deviation of the mean. P-values smaller or equal to 0.05 were considered statistically significant.

Results

CPCL2 and CPCL18 were further characterized based on their cell surface marker profiles using flow cytometry (FIG. 4A-B). Both cell lines were positive for several mesenchymal progenitor markers including CD29, CD49c, CD105, CD166. However, CPCL2 was mostly negative for CD90, whereas CPCL18 had a larger proportion of cells that were positive for this mesenchymal progenitor marker. Collective analysis of multiple flow cytometry experiments demonstrate that CD90 was consistently expressed by >60% of cells in CPCL18, whereas it was only expressed by <20% of cells in CPCL2 (FIG. 4C). Both lines were negative for RM-MSC-specific marker SSEA4 and positive for CD54, a marker that is constitutively expressed by chondrocytes but lowly expressed by MSCs. Lastly, both cell lines were negative for chondrocyte cell surface marker CD106. They also indicate that, in addition to significant differences in PRX1 expression, CPCL2 and CPCL18 may also be distinguished based on the proportion of cells that are CD90+. These results demonstrate that, while both CPC lines exhibited mesenchymal progenitor marker profiles, they also lost certain MSC markers and gained certain chondrocyte cell surface markers (FIG. 4).

The only cell surface marker that quantitatively distinguished CPCL2 from CPCL18 was Thy-1 membrane glycoprotein (CD90). CD90 was mostly negative in CPCL2 (FIG. 4A, FIG. 4C), and mostly positive in CPCL18 (FIG. 4B, FIG. 4C). CD90 was consistently expressed by more than 60% of CPCL18 cells, whereas it was only expressed by less than 20% of CPCL2 cells (FIG. 4C). Furthermore, there was a quantitative decrease of CD90 expression levels from BM-MSCs (97%), CPCL18 (60%), CPCL2 (18%), to PHCs (<10%). In contrast, similar to BM-MSCs, both CPC lines shared high expression levels of CD49c and CD166 (FIG. 4C). On the other hand, similar to PHCs, both lines exhibited high expression levels of CD54 (FIG. 4C). Overall, these results indicate that both cell lines express a combination of mesenchymal progenitor cell surface markers and chondrocyte cell surface markers that uniquely distinguish them from MSCs and chondrocytes.

Example 4: Multipotent Differentiation Potentials of Cartilage-Derived Progenitor Cell Lines This Example determines the chondrogenic, osteogenic and adipogenic differentiation capacities of cartilage-derived progenitors cell lines.

Materials and Methods

Cartilage-derived progenitor lines were assessed for their chondrogenic, osteogenic and adipogenic differentiation potential. For chondrogenesis, $2.5 \times 10^5$ viable cells were centrifuged at 300×g for 10 min in a 15 mL conical tube. The cell pellet was cultured in 1.0 mL of Stempro® Chondrocyte Differentiation Media (Life technologies, Grand Island, N.Y., USA) containing gentamicin (5.0 µg/mL). Media was changed every 3 days making sure as not to disturb cell pellet. After 21 days, cell pellets were fixed in formalin, paraffin embedded and sectioned into 3.0 µm thick sections. The sections were mounted onto slides, cleared with xylene and rehydrated using sequential incubation in 100%, 95%, 70% and 50% ethanol solution prior to staining with Safranin-O. Images of pellet sections were taken using a Nikon Eclipse 90i microscope at 20× magnification. For osteogenesis, $5.0 \times 10^3$ viable cells were seeded into single wells of 12-well cell culture plates and cultured using Stempro® Osteogenesis differentiation media (Life technologies, Grand Island, N.Y., USA) containing gentamicin (5.0 µg/mL) according to the manufacturer's instructions. For osteogenesis, $5.0 \times 10^3$ viable cells were seeded into single wells of 12-well cell culture plates. Media was changed every 3-4 days and cells were stained using Alizarin Red after 21 days in monolayer culture. Images were taken using a Leica MZ6 dissecting microscope at 4× magnifications. For adipogenesis, $5.0 \times 10^4$ cells were seeded into a single well of a 6-well plate and cultured using Stempro® Adipogenesis differentiation media (Life technologies, Grand Island, N.Y., USA) containing gentamicin (5.0 µg/mL) according to the manufacturer's instructions. Media was changed every 4 days and cells were stained Oil Red-O and hematoxylin after 21 days in monolayer culture. Images were taken using a Nikon Eclipse TE2000 inverted microscope at 20× magnification.

Chondrogenic, osteogenic and adipogenic differentiation potential was also assessed in these two cell lines using mRNA expression analysis via RT-PCR. Cells were cultured under the same conditions described above and mRNA was collected in growth medium or differentiation medium. As previously described, gene expression analysis was conducted using real-time PCR. Total mRNA was isolated from cells using an RNAqueous Kit (Ambion, Austin, Tex., USA) according to manufacturer's instructions. mRNA was reverse transcribed using iScript cDNA Synthesis Kit (Bio-Rad, Hercules, Calif., USA) according to the manufacturer's instructions. Table 1 lists the forward and reverse primer sequences used to conduct gene expression analysis in this study. Ribosomal RNA (rRNA) 18S was used as the housekeeping gene for normalization. mRNA transcript levels were calculated using the delta delta Ct (ΔΔCt) method, normalized to rRNA 18S expression as follows: $X=2-\Delta\Delta Ct$, in which $\Delta\Delta Ct=(CtExp-Ct18S)-(CtCtl-Ct18S)$ and X=Relative transcript; CtCtl=Ct of control group. Statistics were performed using either one-way analysis of variance (ANOVA) followed by post-hoc analysis or a two-tailed Student's t-test to compare induction groups with their respective growth medium treated control groups. All quantitative analyses were conducted using sample sizes of 3 or greater. Error bars represent±one standard deviation of the mean. P-values smaller or equal to 0.05 were considered statistically significant.

Results

The chondrogenic, osteogenic and adipogenic differentiation capacities of CPCL2 and CPCL18 were assessed. Both lines were capable of chondrogenic differentiation as indicated by positive Safranin-O staining following induction with chondrogenesis medium (FIG. 5A). CPCL2 exhibited noticeably higher Safranin-O staining upon induction (FIG. 5A). Gene expression analysis confirmed that mRNA levels of chondrogenesis markers ACAN, COL2A1 and SOX9 were elevated in both cell lines following induction with chondrogenesis medium (FIG. 5B top). As shown in FIG. 5B (bottom), collagen X expression is elevated in both cell lines following chondrogenic differentiation. FIG. 5C indicates that matrix metalloproteinase 13 (MMP-13) is elevated in both cell lines, following chondrogenic differentiation. Since both collagen X and MMP-13 are markers of chondrocyte hypertrophy, a hallmark of osteoarthritis, this indicates that these stem cells from osteoarthritis patients have osteoarthritis disease phenotypes, which may contribute to OA pathogenesis. However, relative to CPCL2, CPCL18 exhibited a more robust response to osteogenic induction medium as indicated by Alizarin Red staining (FIG. 5D) and mRNA expression analysis of alkaline phosphatase (ALPL) (FIG. 5D). While ALPL was induced in both cell lines in response to induction with osteogenic medium, CPCL18 exhibited an 11-fold induction of this marker, relative to the 4-fold induction observed in CPCL2 (FIG. 5E). Both cell lines exhibited moderate Oil Red O staining in response to induction with adipogenic medium indicating that both cell lines are capable of undergoing a limited degree of adipogenesis (FIG. 5F). Likewise, adipogenesis marker lipoprotein lipase (LPL) was elevated in a similar manner in both cell lines (FIG. 5G). Taken together, these results demonstrate CPCL2 has a more limited capacity to differentiate along the osteogenic lineage, relative to CPCL18. Hence, these findings indicate that CPCL2 may have been derived from a chondroprogenitor cell that is highly committed to the chondrogenic lineage, whereas CPCL18 came from a cell that can be more accurately described as an osteochondral-progenitor due to its differentiation along the chondrogenic lineage as well as its robust differentiation along the osteogenic lineage.

Cell proliferation rate (CPR) was quantified in both CPC lines. CPCL2 had a three-fold higher CPR than that of CPCL18 in CPC growth medium (FIG. 4G), which was consistent with the higher CFE of the primary CPC from which CPCL2 was derived. Induction of osteogenesis increased the CPR by 11.3 fold in the CPCL18 cells in comparison to the 2.1-fold CPR increase in the CPCL2 cells, indicating the CPCL18 cells were preferentially activated by osteogenic conditions (FIG. 5H). Taken together, these results demonstrated the multi-potency of cell differentiation in both CPC lines. CPCL2 had a robust chondrogenic potential and a limited capacity to differentiate along the osteogenic lineage, while CPCL18 had a robust osteogenic potential but remained very slow growth under non-osteogenic conditions.

Example 5: In Situ Identification of CPCs in Human OA Articular Cartilage

To perform in vivo validation of the CPCs identified by in vitro analysis, immunohistochemistry and Fluorescently Activated Cell Sorting (FACS) experiments were conducted using human OA articular cartilage.

Materials and Methods

FACS was performed as described above.

For immunohistochemistry, human OA cartilage sections were fixed overnight in formalin solution and paraffin embedded. The blocks were then sectioned (3.0 µm thick), mounted onto slides, cleared with xylene and rehydrated using sequential incubation in 100%, 95%, 70% and 50% ethanol solution. Sample slides were rinsed in deionized water and antigen retrieval was performed using sodium citrate buffer (10 mM sodium citrate, pH 6) and an 850W microwave. Slides were blocked overnight at 4° C. using 1% bovine serum albumin in 1×PBS to eliminate non-specific binding of the primary antibody. Slides were stained with a monoclonal mouse antibody (diluted 1:100 in 1×PBS, 1% BSA) against human CD166 (Abeam, Cambridge, Mass., USA) or human PRG4, overnight at 4° C. Sections were then stained for 30 min with a green fluorescently labeled anti-mouse secondary antibody Alexa Fluor ab150105 (Abcam, Cambridge, Mass., USA). Fluorescent images were acquired at 20× magnification using a Nikon Eclipse 90i Digital Imaging System.

Statistics were performed using a two-tailed Student's t-test. All quantitative analyses were conducted using sample sizes of 3 or greater. Error bars represent±one standard deviation of the mean. P-values smaller or equal to 0.05 were considered statistically significant.

Results

Cell surface marker analysis indicated that CD166 is one of the markers highly expressed by both CPCL2 and CPCL18 (FIG. 4), which was consistent with previous observations. On the other hand, gene expression analysis of molecular markers of CPCs indicated PRG4 was expressed at very low levels in the CPCs of both lines (FIG. 3E). This was unexpected given implications of previous studies. Immunofluorescent histochemistry analysis indicated that CD166 was expressed specifically by cells in the superficial zone and the top of the middle zone in the full thickness of human OA articular cartilage (FIG. 8A). Four specimens of OA cartilage from different patients was stained for CD166 and less than 5% of all cells in the full cartilage thickness were observed to be positive for this cell surface marker, in every patient. In contrast, PRG4 was distributed only at the articular surface of human OA cartilage, but not within the cartilage tissue (FIG. 8B). These in vivo observations were consistent with the gene expression data from the CPC lines.

To validate that CD166+ cells were indeed CPCs as seen in immunofluorescent histochemistry analysis, CD166+ cells were isolated from human OA articular cartilage through FACS using an antibody specific for CD166. These CD166+ cells exhibited significantly lower expression of chondrogenic markers ACAN and COL2A1 mRNA and increased expression of a fibronectin receptor CD49e in comparison to CD166− cells in human cartilage in vivo (FIG. 8D). These observations were consistent with the comparison of these markers between primary CPCs and PHCs (FIG. 2A). They were also consistent with the comparison between the CPC lines and PHCs (FIG. 2B-FIG. 2D). These data support the conclusion that the CPC lines were indeed derived from primary CPCs that reside in human OA articular cartilage and retained their characteristics in vitro.

Chondroprogenitor cells have been shown to exist at various sites in the joint and surrounding tissue including bone and bone marrow, infrapatellar fat pad, synovium, perichondrium and articular cartilage. However, their number is very low, especially in adult articular cartilage. Their limited availability presents a challenge for research endeavors seeking to better characterize these cells. Cellular, molecular and functional characteristics of cartilage-derived chondroprogenitor cells were evaluated. To achieve this goal, large quantities of clonally derived chondroprogenitor cells are required. Multiple stable cell lines were generated. Each line originated from a colony of 32 or more cells originating from different individual chondroprogenitor cells derived from human OA cartilage.

The mesenchymal progenitor cells in the joint may contain a variety of cells with different capacities for multi-lineage cell differentiation. For example, MSCs are the stem cells of mesenchymal origin that can differentiate into multi-lineage cells including chondrocytes, osteoblasts and adipocytes. BM-MSCs are the best-studied mesenchymal progenitor cells. They were used as a control in this study to determine whether the adult articular cartilage-derived progenitor cells were identical or similar to BM-MSCs. On the other hand, OCPs are the progeny of MSCs that have a tendency to differentiate into chondrocytes and osteoblasts. A good example of OCPs are the progenitor cells in the bone fracture callus, which contribute to both endochondral as well as intramembranous ossification during fracture healing. In contrast, chondroprogenitors are the cells that have preferred tendency to differentiate into chondrocytes. In comparison to MSCs or OCPs, chondroprogenitors are prone to undergo chondrogenesis upon induction, rather than differentiating along other cell lineages. A good example of chondroprogenitors is the chicken limb bud mesenchymal cells, which undergo chondrogenesis upon condensation. The ATDC5 cell line, which was derived from mouse tetratocarcinoma, has been widely used for chondrogenesis studies. In this study, multiple human chondroprogenitor cell lines from adult OA articular cartilage were generated. These novel cell lines are valuable for understanding the unique properties of chondroprogenitor cells in human OA articular cartilage and for therapeutic use to heal and/or regenerate cartilaginous and/or osseous tissue.

Several characteristic features distinguish these chondroprogenitor cells from mature articular chondrocytes. First, the gene expression profiles of chondroprogenitors are different from chondrocytes, although they reside side-by-side in articular cartilage. Reduced chondrocyte marker (COL2A1, ACAN) expression and increased expression of fibronectin receptor CD49e are hallmarks distinguishing the chondroprogenitor cell lines from chondrocytes. Some cell lines exhibited higher basal expression of chondrocyte markers than others. This result indicates that such cell lines originated from cells that were further differentiated along the chondrogenic lineage and are therefore more similar to chondrocytes than the cell lines exhibiting lower basal expression of chondrocyte markers. Second, these chondroprogenitors do not express CD106, a marker expressed by articular chondrocytes. Third, the expression levels of chondrogenic markers matrilin-3, SOX9 and PRG4 in chondroprogenitors were low similar to that of BM-MSCs rather than articular chondrocytes. Particularly surprising was the finding that both chondroprogenitor cell lines CPCL2 and CPCL18 exhibited low expression of PRG4, which has been proposed to be highly expressed by chondroprogenitors in the superficial zone during mouse articular cartilage development. Since these cell lines were generated using chondroprogenitor cells from adult human articular cartilage, such difference in PRG4 expression was due to the difference between developing and adult cartilage, or the species difference between mouse and human. Alternatively, reduced expression of PRG4 in these cells is a pathogenic feature of OA, since these cells are derived from OA patient cartilage.

Characteristic features were identified that distinguish these chondroprogenitor cells from MSC. Although these chondroprogenitors share several common markers with BM-MSC including CD29, CD49c, CD105 and CD166, they do not express BM-MSC marker SSEA4. Chondroprogenitor cells express high levels of CD54, which was lowly expressed by MSCs but constitutively expressed by articular. The molecular profiles of these chondroprogenitors indicate that these cells are the progeny of MSCs that have further differentiated along the chondrogenic pathway.

At least two types of molecularly and functionally distinct progenitor cells were derived from adult human OA cartilage. Several features distinguish these two types of chondroprogenitors. First, the analysis revealed that PRX1 mRNA expression level is significantly different between CPCL2 and CPCL18. Compared with CPCL2, CPCL18 exhibited higher basal expression of PRX1 (3-fold increase). It has been shown that cells that constitute the limb mesenchyme during skeletogenesis have elevated PRX1 expression. These mesenchymal precursors are particularly regarded for their plasticity during development. Hence, the higher PRX1 expression level in CPCL18 is consistent with the finding that this line has higher plasticity than CPCL2. Second, the only tested cell surface marker to distinguish the two cell lines is CD90, although both cell lines had remarkably similar cell surface marker profiles including CD29+/CD49c+/CD54+/CD105+/CD106−/CD166+/SSEA4−. CD90 was expressed by a significantly higher proportion of cells in CPCL18, relative to CPCL2. Since CD90 is a mesenchymal progenitor marker, this was consistent with the notion that CPCL18 has higher cell lineage plasticity over CPCL2. Third, CPCL18 can undergo osteogenic differentiation upon induction much more robustly than CPCL2, although both cell lines are multi-potent. In addition, CPCL18 cells grew very slowly in the CPC growth medium, having less than one quarter of the proliferation rate of CPCL2. However, upon induction of osteogenesis by the osteogenesis medium, the proliferation rate of CPCL18 cells increased by 11.3-fold in comparison to the 2.1-fold increase by CPCL2. Thus, osteogenic conditions preferentially activate the growth of CPCL18 cells. These data indicate that CPCL18-like progenitor cells lay dormant in adult articular cartilage until activation by osteogenic conditions. Such conditions may occur during injury such as fracture or trauma, which would lead to the growth of the CPCL18 cells and activation of the osteogenesis pathway in adult articular cartilage. At least some of the osteophytes, a hallmark of osteoarthritis, may originate from the growth and osteogenesis of the CPCL18-like progenitors in articular cartilage. Taken together, these findings indicate that CPCL2 and CPCL18 cells are different types of progenitor cells from human articular cartilage. While CPCL2 is a chondroprogenitor cell line, CPCL18 can be better described as an osteochondral-progenitor cell line.

The existence of these two types of CPCs is not an isolated incident since there are multiple cell lines in both Group I and Group II CPCs (FIG. 2B-D). These two groups of CPCs may represent two different mesenchymal progenitor cell lineages or rather two different stages of maturation/differentiation along the same lineage. According to the "two-lineage" system, the cells that are currently collectively described as CPCs actually consist of inherently different cell lineages that are destined to become osteoblasts and chondrocytes respectively (FIG. 9). Thus, CPCs such as CPCL2 are more suitable for cell-based cartilage repair, while OCPs such as CPCL18, which are prone to growth activation and osteogenesis by osteogenic stimuli, should be inhibited during the treatment of osteoarthritis. Conversely, a "two-stage" hypothesis involves multiple differentiation stages that exist during the maturation process of MSCs to become chondrocytes (FIG. 9). To enhance cartilage repair, one cannot simply inhibit OCPs such as CPCL18 because that will reduce the number of progeny cells during chondrogenesis process. Instead, one modulates the cell differentiation process by enhancing chondrogenic potential and/or suppressing osteogenic potential of the OCPs, resulting in generation of more chondrogenic progeny cells including CPCL2-like CPCs as well as mature chondrocytes.

The cell lines described herein retain key features of CPCs including their inherent gene expression profile and cellular functions. The cell and molecular properties of the cell lines were validated by comparing them to primary CPCs as well as to CPCs residing in adult human cartilage in vivo. These cell lines retain the expression profiles of both primary CPCs isolated from human cartilage as well as those residing in cartilage. The CPCs of three sources (cell line, primary and in situ) express the same gene expression profiles including the lower levels of chondrogenic markers such as COL2A1 and the higher levels of fibronectin receptor CD49e than mature chondrocytes. In addition, the cell lines are CD105+CD166+, which is one of the important criteria established previously for identification of CPCs in human articular cartilage. Based on analysis of the CPC lines, the cells with the same protein marker profiles (CD166+PRG4−) were localized in the superficial zone and the top of middle zone in human adult articular cartilage, the same area where CPCs were identified previously. These CPC lines were multi-potential capable of chondrogenesis, osteogenesis and adipogenesis, thus possessing the same multi-potency as the CPCs in the tissue. Finally, genetic profiling of these cell lines indicate that the CPC lines generated from different patients have similar gene expression characteristics, thus excluding any individual differences.

In summary, generation of multiple CPC cell lines, as described here, has enabled detailed analysis and characterization of clonally derived progenitor cells from human articular cartilage for various uses such as therapy for degenerative diseases as well as fractures of cartilaginous and/or osseous tissue, and/or bone spurs. It resulted in the discovery that multiple lineages (or stages) of CPCs may co-exist in human adult osteoarthritic cartilage. It provides a powerful tool to analyze the role of CPCs during osteoarthritis pathogenesis as well as for cartilage repair with tissue engineering.

Example 6: Differential Expression of Long Non-Coding RNAs During Chondrogenesis in Human MSCs, Osteochondral-Progenitor Cells, and Chondroprogenitor Cells Long non-coding RNAs (lncRNAs) are classified as transcripts longer than 200 nucleotides without obvious protein-coding function. Over the past decades, emerging evidence has demonstrated only 2% of the human genome codes for protein, while as much as 70-90% of the genome is transcribed to a large transcriptome of lncRNAs. LncRNAs function in a variety of processes and can regulate gene expression by diverse mechanisms. Recent studies have demonstrated the significance of lncRNAs in cell differentiation and development.

In this Example, microarray analysis was performed to identify the lncRNAs differentially expressed during chondrogenesis differentiation of mesenchymal cells (MSCs). Furthermore, lncRNA expression in human osteochondral-progenitor cell lines and in chondroprogenitor cell lines were examined.

Materials and Methods

Human bone marrow-derived mesenchymal stem cells were purchased from ATCC, while human articular cartilage derived progenitor cell lines were generated in the laboratory. High-density cell culture system, namely micromass culture was used to induce chondrogenic differentiation of hMSCs. Briefly, cells were trypsinized and resuspended in chondrogenic medium (DMEM supplemented with Dexamethasone (10-7 M), Ascorbic acid-2-phosphate (50 µg/ml), TGF-β1 (10 ng/ml), ITS+1 Liquid Media Supplement (1.0 mg/ml bovine insulin, 0.55 mg/ml human transferrin, 0.5 µg/ml sodium selenite, 50 mg/ml bovine serum albumin and 470 µg/ml linoleic acid at the 100× concentration), at a density of 2×107 cells/ml. Cells were harvested at day 21. Chondrogenic differentiation was assessed by Alcian Blue staining. Total RNA was extracted with Trizol Reagent following the manufacturer's instructions. Each sample was amplified and transcribed into fluorescent cRNA along the entire length of the transcripts without 3' bias utilizing a random priming method (Arraystar Flash RNA Labeling Kit, Arraystar). The labeled cRNAs were hybridized onto the Human LncRNA Array v3.0 (8×60K, Arraystar). After having washed the slides, the arrays were scanned by the Agilent Scanner G2505C. Quantitative Real-time PCR was utilized to verify the reliability of the microarray data and to examine the expression levels of lncRNAs and mRNAs in chondrogenic progenitor cells.

Results

Through lncRNA microarray analysis a spectrum of lncRNAs were identified to be differentially expressed during chondrogenesis of human mesenchymal stem cells. 4338 differentially expressed lncRNAs were identified (fold change>2.0 or <−2.0, P<0.05), including 2350 up-regulated and 1988 down-regulated. Eight lncRNAs, which were either up- or down-regulated during chondrogenesis but remained unchanged during osteogenesis or adipogenesis, were chosen for further analysis. The expression patterns of these lncRNAs were validated by qRT-PCR, which were consistent with microarray data. Five lncRNAs including 10324, 16208, 83436, 5441, and 30545, were up-regulated during chondrogenesis of MSC, while three lncRNAs including TVAS5, FAM86, CTA, were down-regulated during chondrogenesis of MSC (FIG. 6A). Both osteochondral-progenitor cells (Line 18) and chondroprogenitor cells (Line 2) undergo chondrogenesis upon induction. However, the extent of chondrogenesis in chondroprogenitor cells (L2) is significantly stronger than osteochondral-progenitor cells (L18) as measured by the expression levels of chondrogenic markers collagen II, aggrecan, and Sox9 mRNA levels (FIG. 6B). Three lncRNAs (FAM86, 10324 and TVAS5) were specifically expressed in L2 cells, but not expressed in L18 cells. Interestingly, the lncRNA expression pattern during chondrogenesis of L2 chondroprogenitor cells was the same as MSCs (FIG. 6C). During chondrogenesis of L18 osteochondral-progenitor cells, only CTA was down-regulated and lncRNA 16208, 83436, 5441, and 30545 were up-regulated.

These findings represent the first evidence that lncRNAs changed their expression patterns during MSC chondrogenesis differentiation. Without being bound to theory, this indicates that these lncRNAs may play a role in chondrogenesis process of MSCs. Since some lncRNAs were up-regulated and some were down-regulated, they may play a positive or negative role during chondrogenesis. lncRNAs expression patterns were also found to be different between osteochondral-progenitor cells and chondroprogenitor cells. Therefore, three lncRNAs including TVAS5, FAM86, and 10324 can be used to distinguish chondroprogenitor cells from osteochondral-progenitor cells. Furthermore, again without being bound to theory, the data indicates that these three lncRNAs were not required for chondrogenesis in osteochondral-progenitor cells.

Example 7: Propagation of Cartilage-Derived Stem Cells in OA Cartilage

This example shows that stem cells are actively undergoing propagation in cartilage obtained from individuals with osteoarthritis.

Materials and Methods

Patients. Patient tissues were acquired and used in accordance with the Institutional Review Board (IRB) of Rhode Island Hospital. OA-SCs were isolated from human osteoarthritic articular cartilage. Cells from a male and female patient undergoing total knee replacement surgery were pooled together in order to generate multiple cell lines.

Human chondrocytes utilized in this study were freshly isolated from OA articular cartilage obtained from complete joint replacement surgeries. OA cartilage-derived cells were isolated from the full thickness of articular cartilage and did not contain lesions or exhibit tissue discoloration.

Cell culture. Dulbecco's Modified Eagle Medium (DMEM), fetal bovine serum (FBS), Hank's Balanced Salt Solution (HBSS) and Penicillin Streptomycin (Pen Strep) were purchased from Life Technologies, Grand Island, N.Y. Chondrocytes were grown using DMEM supplemented with 10% FBS and 1% Pen Strep. Cell lines were maintained in DMEM supplemented with 10% FBS, 1% Pen Strep, 100 mM HEPES, 2 mM L-glutamine, 0.1 mM ascorbic acid, 0.1 mM sodium pyruvate, 0.5 mg/mL L-glucose (DMEM+). All cells were grown in a 37° C. cell culture incubator.

Isolation and enrichment of cartilage-derived progenitor cells. Cells were isolated from the entire thickness of articular cartilage. Samples were washed three times with 1×HBSS diced into small fragments. The diced cartilage tissue was treated with Pronase (Roche, Indianapolis, Ind., USA) in 1×HBSS (2.0 mg/mL) for 30 minutes in a 37° C. shaking water bath. Cartilage fragments were then washed twice with DMEM and further digested with Type IA Crude Bacterial Collagenase (Sigma-Aldrich, St. Louis, Mo., USA) (1.0 mg/mL) for 8 hrs in a 37° C. shaking water bath. Cells were strained through a 100 µm nylon cell strainer (BD, Franklin Lakes, N.J., USA) to remove clumps and washed three times with 5.0 mL of DMEM supplemented with 10% FBS. Cells were then counted using a hemacytometer. Cartilage-derived progenitors were enriched using differential cell adhesion to fibronetin similar to a previously described method (Williams, et al., 2010). Cells (2000 cells/mL) were plated in 60 mm dishes that had been coated at 4° C. overnight with 10 µg/mL of fibronectin in 0.1 M PBS containing 1.0 mM MgCl and 1.0 mM $CaCl_2$. Cells were seeded and left for 20 min at 37° C. After 20 mM, non-adherent cells were removed from the plates and fresh DMEM+ was added. Adherent cells were observed and counted under a light microscope. Approximately after 2 weeks, single cells that had formed individual colonies consisting of ≥32 cells were isolated using glass cloning cylinders (Sigma-Aldrich, St. Louis, Mo., USA), taking care not to cross contaminate with cells from neighboring regions, and reseeded in individual wells of 6-well cell culture plates. Colonies were cultured for one week.

Generation of stable OA cartilage-derived chondroprogenitor cell lines. After one week in culture, these clonally derived cell colonies were treated with a retroviral vector pRetro-E2 SV40 (Applied Biological Materials Inc., Richmond, BC, Canada). According to the manufacturer's instructions, colonies were then continuously expanded for two months (>20 passages) until only the successfully transformed cells remained. Each cell line was genotyped/profiled for authenticity using autosomal short tandem repeat (STR) loci analysis (Genetica DNA Laboratories, Burlington, N.C., USA).

Real-time PCR. Gene expression analysis was conducted using real-time PCR. Total messenger RNA (mRNA) was isolated from cells using a RNAqueous Kit (Ambion, Austin, Tex., USA) according to manufacturer's instructions. mRNA was reverse transcribed using iScript cDNA Synthesis Kit (Bio-Rad, Hercules, Calif., USA) according to the manufacturer's instructions. Supplementary table 1 lists forward and reverse primer sequences used to conduct gene expression analysis. Ribosomal RNA (rRNA) 18S was used as the housekeeping gene for normalization. mRNA transcript levels were calculated using the delta delta Ct (ΔΔCt) method, normalized to rRNA 18S expression as follows: X=2-ΔΔCt, in which ΔΔCt=(CtExp−Ct18S)−(CtCtl−Ct18S) and X=Relative transcript; CtCtl=Ct of control group.

Flow cytometry. Pre-conjugated antibodies CD49c-APC and CD166-PE were purchased from BioLegend, San Diego, Calif., USA. SSEA4-PE, CD29-APC, CD54-PE, CD90-FITC, CD105-APC, CD106-APC were purchased from Miltenyi Biotec Inc., San Diego, Calif., USA. Isotype IgG control antibodies were also purchased from Miltenyi Biotec Inc. Cells to be stained were washed 2 times with 5.0 mL of sterile HBSS and detached using 2.0 mL of TrypLE Express (Life Technologies, Grand Island, N.Y., USA). Cells were washed with DMEM supplemented with 10% FBS and spun down using a centrifuge set for 300×g. Cells were washed once again with 5.0 mL sterile 1×PBS and spun down at 300×g. Viable cell number was quantified using a hemacytometer and 0.4% Trypan blue solution (Life Technologies, Grand Island, N.Y., USA). For each sample to be stained, $1.0 \times 10^6$ viable cells were resuspended in 100 µL of Flow buffer (1x PBS, pH 7.2, 0.5% bovine serum albumin and 2 mM EDTA). Pre-conjugated antibody (10 µL) was added to the resuspension, mixed and incubated for 10 min in the dark at 4° C. Cells were washed 3 times with 1.0 mL of 1×PBS and resuspended in 500 mL of Flow buffer before single channel FACS analysis using an Accuri C6 Flow Cytometer (BD Biosciences, San Jose, Calif., USA). Control experiments for non-specific staining using mouse IgG were performed alongside all experiments.

Differentiation assays. Cell lines were assessed for their chondrogenic, osteogenic and adipogenic differentiation potential. For chondrogenesis, $2.5 \times 10^5$ viable cells were centrifuged at 300×g for 10 min in a 15 mL conical tube. The cell pellet was cultured in 1.0 mL of Stempro® Chondrocyte Differentiation Media (Life technologies, Grand Island, N.Y., USA) containing gentamicin (5.0 µg/mL). Media was changed every 3 days making sure not to disturb cell pellet. After 21 days, cell pellets were fixed in formalin, paraffin embedded and sectioned into 3.0 µm thick sections. The sections were mounted onto slides, cleared with xylene and rehydrated using sequential incubation in 100%, 95%, 70% and 50% ethanol solution prior to staining with Safranin-O. Images of pellet sections were taken using a Nikon Eclipse 90i microscope at 20× magnification. For osteogenesis, $5.0 \times 10^3$ viable cells were seeded into single wells of 12-well cell culture plates and cultured using Stempro® Osteogenesis differentiation media (Life technologies, Grand Island, N.Y., USA) containing gentamicin (5.0 µg/mL) according to the manufacturer's instructions. For osteogenesis, $5.0 \times 10^3$ viable cells were seeded into single wells of 12-well cell culture plates. Media was changed every 3-4 days and cells were stained using Alizarin Red after 21 days in monolayer culture. Images were taken using a Leica MZ6 dissecting microscope at 4× magnification. For adipogenesis, $5.0 \times 10^4$ cells were seeded into a single well of a 6-well plate and cultured using Stempro® Adipogenesis differentiation media (Life technologies, Grand Island, N.Y., USA) containing gentamicin (5.0 µg/mL) according to the manufacturer's instructions. Media was changed every 4 days and cells were stained Oil Red-O and hematoxylin after 21 days in monolayer culture. Images were taken using a Nikon Eclipse TE2000 inverted microscope at 20× magnification.

Immunohistochemistry. Human OA cartilage sections were fixed overnight in formalin solution and paraffin embedded. The blocks were then sectioned (3.0 µm thick), mounted onto slides, cleared with xylene and rehydrated using sequential incubation in 100%, 95%, 70% and 50% ethanol solution. Sample slides were rinsed in deionized water and antigen retrieval was performed using sodium citrate buffer (10 mM sodium citrate, pH 6) and an 850W microwave. Slides were blocked overnight at 4° C. using 1% bovine serum albumin in 1×PBS to eliminate non-specific binding of the primary antibody. Slides were stained with a monoclonal mouse antibody (diluted 1:100 in 1×PBS, 1% BSA) against human CD166 (Abeam, Cambridge, Mass., USA) or human PRG4 (provided by Dr. Gregory Jay), overnight at 4° C. Sections were then stained for 30 min with a green fluorescently labeled anti-mouse secondary antibody Alexa Fluor ab150105 (Abeam, Cambridge, Mass., USA). Fluorescent images were acquired at 20× magnification using a Nikon Eclipse 90i Digital Imaging System.

Statistics. Statistics were performed using a Student's t-test when analyzing two groups or one-way analysis of variance (ANOVA) followed by post-hoc analysis when analyzing more than two groups. Error bars represent±one standard deviation of the mean. P-values smaller or equal to 0.05 were considered statistically significant.

Results

Patient tissue sections obtained from 3 different osteoarthritis (OA) patients were histologically graded using the OARSI scoring system. The percentage of the CD166+ stem cells was 10.5%-21.38% with patient tissue with more severe OA (Grade 2) also contained a larger percentage of stem cells (Table 3). Without being bound to theory, it was hypothesized that greater numbers of stem cell can be found in clusters in OA cartilage, indicating that these stem cells are undergoing self-renewal (FIG. 10A). While the number of CD166-chondrocytes is relatively evenly distributed in single, 2-cell, 3-cell and greater than 3-cell clusters, the number of CD166+ stem cells increases in 3-cell clusters in OA cartilage (FIG. 10B-FIG. 10D). Overall, these findings indicate that stem cells are actively undergoing propagation in OA cartilage.

TABLE 3

Percentages of CD166+ cells in cartilage from patients with OA.

| Patient 1 | | Patient 2 | |
|---|---|---|---|
| Zone | % CD166+ cells | Zone | % CD166+ cells |
| Superficial | 1.50% | Superficial | 9.03% |
| Intermediate | 8.50% | Intermediate | 4.83% |
| Deep | 0.50% | Deep | 1.68% |
| Sum | 10.50% | Sum | 15.55% |
| Zone | % CD166− cells | Zone | % CD166− cells |
| Superficial | 17.25% | Superficial | 19.33% |
| Intermediate | 54.25% | Intermediate | 31.72% |
| Deep | 18.00% | Deep | 33.40% |
| Sum | 89.50% | Sum | 84.45% |

| Patient 3 | |
|---|---|
| Zone | % CD166+ cells |
| Superficial | 11.14% |
| Intermediate | 7.68% |
| Deep | 2.56% |
| Sum | 21.38% |

TABLE 3-continued

Percentages of CD166+ cells in cartilage from patients with OA.

| Zone | % CD166− cells |
|---|---|
| Superficial | 13.25% |
| Intermediate | 34.63% |
| Deep | 30.73% |
| Sum | 78.62% |

Example 8: Generation and Characterization of Cartilage-Derived Chondroprogenitors Derived from Individuals with Osteosarcoma and Use of Same for Soft Tissue Repair This Example describes the generation of chondroprogenitor cell lines from cartilage tissue isolated from an osteosarcoma patient.

Materials and Methods

Nine new chondroprogenitor cell lines originating from non-arthritic patient articular cartilage were generated. These new cell lines were generated in the same manner as those previously created as described in Example 1, with the exception that these new cell lines come from cartilage tissue isolated from an osteosarcoma patient that required amputation. The cartilage was obtained from the knee. Eight out of the nine newly generated cell lines (nCPCL 2-6B) were characterized using mRNA expression analysis of several genes, including chondrogenesis and hypertrophy genes according to the methods discussed above.

Results

Master regulator of chondrogenesis SOX-9 levels in most of these cell lines exceed that of bone marrow-derived mesenchymal stem cells (BM-MSCs) but remain lower than that which is observed in mature chondrocytes (FIG. 11A). Aggrecan expression is variable in these cell lines; however, they are all lower than that of chondrocytes (FIG. 11B) confirming that they are indeed distinct from chondrocytes. Unlike the previously created chondroprogenitor cell lines from osteoarthritic (OA) cartilage described above in Example 1, nCPCL 2-6B cells exhibit higher expression of type I collagen than chondrocytes (FIG. 11C). Without being bound to theory, these data suggest that high type I collagen expression is a key distinctive feature of chondroprogenitor cell lines generated from non-diseased tissue. PRX1 expression is lower in these cell lines compared to both BM-MSCs and chondrocytes (FIG. 11D). Type X collagen is significantly lower in these cell lines than both BM-MSCs and chondrocytes (FIG. 11E).

Next, whether the newly generated nCPC lines can function for cell-based meniscus repair was tested, considering that these cell lines exhibit high expression of type I collagen, moderate level of type II collagen and extremely low levels of type X collagen (see FIG. 11). Cartilage-derived progenitor cells (and cell lines) have been shown to be promising for cell-based meniscus repair strategies. FIG. 12A shows that CD90−/CD105+/CD166+ cartilage-derived stem cells can adhere to the inner avascular surface of the meniscus. Fluorescently labeled CD90−/CD105+/CD166+ cartilage-derived stem cells were seeded into wells containing a decellularized rat menisci. Within 2-days, the cells showed adherence to the inner meniscus (FIG. 12B). After 4-weeks of culture, the decellularized menisci were sectioned, stained with DAPI and imaged to visualize the location of the adherent cells (FIG. 12C). The results indicate that by 4-weeks, these cells have entered the inner avascular region of the meniscus, successfully integrated into the tissue and enhanced proteoglycan content (indicated by positive Saf-O staining) within the inner meniscus (FIG. 12D). Taken together, these findings indicate that CD90−/CD105+/CD166+ cartilage progenitors hold promise for use in cell-based meniscus repair strategies. Next, $5.0\times10^5$ cartilage-derived progenitor cells and $5.0\times10^5$ BM-MSCs were fluorescently labeled and cultured with a rat meniscus containing a radial incision (FIG. 13A, left, indicated by arrowhead and circumscribed in white) for 72 hours in a 96-microwell plate. The cells appeared to migrate to area of the incision (FIG. 13A, right). Further, mRNA expression analysis indicates that human collagen I gene expression levels between cartilage-derived progenitor cells and BM-MSCs, following 4-week culture in meniscus, is comparable. There is no significant difference between collagen I expression by these cells (FIG. 13B). However, collagen X expression is significantly higher in the BM-MSC group (FIG. 13C).

---

The invention claimed is:

1. A stable human chondroprogenitor cell line or stable human osteochondroprogenitor cell line that expresses at least five times less lubricin (PRG4) relative to chondrocytes derived from healthy adult tissue, wherein:
 (a) the cell line expresses at least three times less matrilin 3 (MATN3) relative to chondrocytes derived from healthy adult tissue,
 (b) the cell line expresses two times less type I collagen (COL1) relative to bone marrow-derived mesenchymal stem cells (BM-MSCs);
 (c) the cell line expresses the mesenchymal cell surface markers CD29, CD49c, CD105, and CD166;
 (d) the cell line does not express the bone marrow-derived mesenchymal stem cell surface marker SSEA4; and
 (e) the cell line expresses the chondrocyte cell surface marker CD54.

2. The cell line of claim 1, wherein (a) the cell line does not express the chondrocyte cell surface marker CD106; (b) the cell line expresses higher amounts of ACAN relative to BM-MSCs; (c) the cell line expresses less PRX1 and/or Type X collagen relative to BM-MSCs; (d) the cell line is derived from tissue from an individual diagnosed with osteoarthritis (OA); (e) the cell line is derived from tissue from an individual diagnosed with osteosarcoma; or (f) the cell line is derived from tissue from an individual with a cartilage lesion/injury.

* * * * *

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: ACAN Forward

<400> SEQUENCE: 1
accagacggg cctcccagac                                               20

<210> SEQ ID NO 2
<211> LENGTH: 20
<212> TYPE: DNA
<213> ORGANISM: Artificial Sequence
<220> FEATURE:
<223> OTHER INFORMATION: ACAN Reverse

<400> SEQUENCE: 2
acagcagcca caccaggaac                                               20

<210> SEQ ID NO 3
<211> LENGTH: 20
<212> TYPE: DNA
<213> ORGANISM: Artificial Sequence
<220> FEATURE:
<223> OTHER INFORMATION: COL2A1 Forward

<400> SEQUENCE: 3
tgagggcgcg gtagagaccc                                               20

<210> SEQ ID NO 4
<211> LENGTH: 20
<212> TYPE: DNA
<213> ORGANISM: Artificial Sequence
<220> FEATURE:
<223> OTHER INFORMATION: COL2A1 Reverse

<400> SEQUENCE: 4
tgcacacagc tgccagcctc                                               20

<210> SEQ ID NO 5
<211> LENGTH: 20
<212> TYPE: DNA
<213> ORGANISM: Artificial Sequence
<220> FEATURE:
<223> OTHER INFORMATION: CD49e Forward

<400> SEQUENCE: 5
ggcttcaact tagacgcgga                                               20

<210> SEQ ID NO 6
<211> LENGTH: 20
<212> TYPE: DNA
```

```
<213> ORGANISM: Artificial Sequence
<220> FEATURE:
<223> OTHER INFORMATION: CD49e Reverse

<400> SEQUENCE: 6
attcaatggg ggtgcactgt                                              20

<210> SEQ ID NO 7
<211> LENGTH: 21
<212> TYPE: DNA
<213> ORGANISM: Artificial Sequence
<220> FEATURE:
<223> OTHER INFORMATION: SOX9 Forward

<400> SEQUENCE: 7
ggaccagtac ccgcacttgc a                                            21

<210> SEQ ID NO 8
<211> LENGTH: 24
<212> TYPE: DNA
<213> ORGANISM: Artificial Sequence
<220> FEATURE:
<223> OTHER INFORMATION: SOX9 Reverse

<400> SEQUENCE: 8
gttcttcacc gacttcctcc gccg                                         24

<210> SEQ ID NO 9
<211> LENGTH: 21
<212> TYPE: DNA
<213> ORGANISM: Artificial Sequence
<220> FEATURE:
<223> OTHER INFORMATION: MATN3 Forward

<400> SEQUENCE: 9
tgagggctac actctgaatg c                                            21

<210> SEQ ID NO 10
<211> LENGTH: 20
<212> TYPE: DNA
<213> ORGANISM: Artificial Sequence
<220> FEATURE:
<223> OTHER INFORMATION: MATN3 Reverse

<400> SEQUENCE: 10
gtgcttcctc agtggctgaa                                              20

<210> SEQ ID NO 11
<211> LENGTH: 22
<212> TYPE: DNA
<213> ORGANISM: Artificial Sequence
<220> FEATURE:
<223> OTHER INFORMATION: PRG4 Forward

<400> SEQUENCE: 11
ttcatctcaa gagctttcct gt                                           22

<210> SEQ ID NO 12
<211> LENGTH: 21
<212> TYPE: DNA
<213> ORGANISM: Artificial Sequence
<220> FEATURE:
<223> OTHER INFORMATION: PRG4 Reverse

<400> SEQUENCE: 12
tgatggtttg agatgctcct g                                            21
```

<210> SEQ ID NO 13
<211> LENGTH: 20
<212> TYPE: DNA
<213> ORGANISM: Artificial Sequence
<220> FEATURE:
<223> OTHER INFORMATION: LPL Forward

<400> SEQUENCE: 13
gacacttgcc acctcattcc                                            20

<210> SEQ ID NO 14
<211> LENGTH: 21
<212> TYPE: DNA
<213> ORGANISM: Artificial Sequence
<220> FEATURE:
<223> OTHER INFORMATION: LPL Reverse

<400> SEQUENCE: 14
agccatggat caccatgaag g                                          21

<210> SEQ ID NO 15
<211> LENGTH: 21
<212> TYPE: DNA
<213> ORGANISM: Artificial Sequence
<220> FEATURE:
<223> OTHER INFORMATION: FABP4 Forward

<400> SEQUENCE: 15
tggaaacttg tctccagtga a                                          21

<210> SEQ ID NO 16
<211> LENGTH: 21
<212> TYPE: DNA
<213> ORGANISM: Artificial Sequence
<220> FEATURE:
<223> OTHER INFORMATION: FABP4 Reverse

<400> SEQUENCE: 16
tcacatcccc attcacactg a                                          21

<210> SEQ ID NO 17
<211> LENGTH: 22
<212> TYPE: DNA
<213> ORGANISM: Artificial Sequence
<220> FEATURE:
<223> OTHER INFORMATION: BGLAP Forward

<400> SEQUENCE: 17
ctggccgcac tttgcatcgc tg                                         22

<210> SEQ ID NO 18
<211> LENGTH: 22
<212> TYPE: DNA
<213> ORGANISM: Artificial Sequence
<220> FEATURE:
<223> OTHER INFORMATION: BGLAP Reverse

<400> SEQUENCE: 18
agccaactcg tcacagtccg ga                                         22

<210> SEQ ID NO 19
<211> LENGTH: 18
<212> TYPE: DNA
<213> ORGANISM: Artificial Sequence
<220> FEATURE:

```
<223> OTHER INFORMATION: PPARG Forward

<400> SEQUENCE: 19
cgtggccgca gaaatgac                                                18

<210> SEQ ID NO 20
<211> LENGTH: 20
<212> TYPE: DNA
<213> ORGANISM: Artificial Sequence
<220> FEATURE:
<223> OTHER INFORMATION: PPARG Reverse

<400> SEQUENCE: 20
aggagtggga gtggtcttcc                                              20

<210> SEQ ID NO 21
<211> LENGTH: 21
<212> TYPE: DNA
<213> ORGANISM: Artificial Sequence
<220> FEATURE:
<223> OTHER INFORMATION: ALPL Forward

<400> SEQUENCE: 21
ctggacggac cctcgccagt g                                            21

<210> SEQ ID NO 22
<211> LENGTH: 22
<212> TYPE: DNA
<213> ORGANISM: Artificial Sequence
<220> FEATURE:
<223> OTHER INFORMATION: ALPL Reverse

<400> SEQUENCE: 22
tgcaatcgac gtgggtggga gg                                           22

<210> SEQ ID NO 23
<211> LENGTH: 20
<212> TYPE: DNA
<213> ORGANISM: Artificial Sequence
<220> FEATURE:
<223> OTHER INFORMATION: PRX1 Forward

<400> SEQUENCE: 23
catcgtacct cgtcctgctc                                              20

<210> SEQ ID NO 24
<211> LENGTH: 22
<212> TYPE: DNA
<213> ORGANISM: Artificial Sequence
<220> FEATURE:
<223> OTHER INFORMATION: PRX1 Reverse

<400> SEQUENCE: 24
gtaaacaaca tcttgggagg ga                                           22
```